US007322969B2

(12) United States Patent
Hattori et al.

(10) Patent No.: US 7,322,969 B2
(45) **Date of Patent: *Jan. 29, 2008**

(54) LIQUID-MEDICINE INJECTION PORT DEVICE, AND LIQUID-MEDICINE CONTAINER PROVIDED WITH THE SAME

(75) Inventors: Hiroyuki Hattori, Uji (JP); Takamitsu Ohkawara, Otsu (JP); Atsushi Ishikawa, Otsu (JP)

(73) Assignee: Nipro Corporation, Osaka (JP)

( * ) Notice: Subject to any disclaimer, the term of this patent is extended or adjusted under 35 U.S.C. 154(b) by 269 days.

This patent is subject to a terminal disclaimer.

(21) Appl. No.: 10/488,462

(22) PCT Filed: Sep. 13, 2002

(86) PCT No.: PCT/JP02/09407

§ 371 (c)(1), (2), (4) Date: Mar. 4, 2004

(87) PCT Pub. No.: WO03/028617

PCT Pub. Date: Apr. 10, 2003

(65) Prior Publication Data

US 2004/0267228 A1 Dec. 30, 2004

(30) Foreign Application Priority Data

Sep. 14, 2001 (JP) ............................ 2001-279182
Aug. 8, 2002 (JP) ............................ 2002-231489

(51) Int. Cl.
*A61M 5/145* (2006.01)
*B65D 85/816* (2006.01)

(52) U.S. Cl. ...................... 604/406; 604/190; 604/405; 206/828

(58) Field of Classification Search ................ 604/406, 604/405, 190, 200; 206/828
See application file for complete search history.

(56) References Cited

U.S. PATENT DOCUMENTS 2,879,207 A * 3/1959 Poitras .................... 435/287.7
3,520,416 A * 7/1970 Keedwell .................... 210/490

(Continued)

FOREIGN PATENT DOCUMENTS

EP 0 696 448 A2 2/1996

(Continued)

*Primary Examiner*—Tatyana Zalukaeva
*Assistant Examiner*—Paula L. Craig
(74) *Attorney, Agent, or Firm*—Kubovcik & Kubovcik

(57) ABSTRACT

A liquid-medicine injection port device includes: a liquid-medicine inlet which is formed at its upper end; a liquid-medicine outlet which is formed at its lower end which is connectable to a liquid-medicine container; a liquid passageway which connects the liquid-medicine inlet and the liquid-medicine outlet; a germ-removal filter which is provided in the liquid passageway; and a closure which closes the liquid passageway downstream from the germ-removal filter and opens it easily. Further, a liquid-medicine container is provided with this liquid-medicine injection port device. Or further, the liquid-medicine container has a two-chamber structure in which an injection chamber provided with the liquid-medicine injection port device which the germ-removal filter is attached to, and a storage chamber storing a liquid medicine are divided by a weak seal portion having such a strength that it is easily peeled.

8 Claims, 27 Drawing Sheets

U.S. PATENT DOCUMENTS

| | | | | | |
|---|---|---|---|---|---|
| 3,709,365 | A | * | 1/1973 | Czaplinski et al. | 210/233 |
| 3,732,981 | A | * | 5/1973 | Mendelsohn | 210/94 |
| 3,803,810 | A | * | 4/1974 | Rosenberg | 96/6 |
| 4,076,027 | A | * | 2/1978 | Koenig | 604/406 |
| 4,093,108 | A | * | 6/1978 | Hein et al. | 222/401 |
| 4,332,249 | A | * | 6/1982 | Joslin | 604/36 |
| 4,997,430 | A | | 3/1991 | Van der Heiden et al. | 604/414 |
| 5,114,240 | A | * | 5/1992 | Kindt-Larsen et al. | 366/129 |
| 5,120,438 | A | * | 6/1992 | Nakagawa et al. | 210/256 |
| 5,662,642 | A | * | 9/1997 | Isono et al. | 604/403 |
| 5,792,425 | A | * | 8/1998 | Clark et al. | 422/101 |
| 6,622,882 | B2 | * | 9/2003 | Smith | 220/259.1 |
| 6,719,745 | B1 | * | 4/2004 | Taylor | 604/406 |
| 6,773,427 | B2 | * | 8/2004 | Takagi | 604/415 |
| 6,959,812 | B2 | * | 11/2005 | Reif et al. | 206/469 |
| 7,029,465 | B2 | * | 4/2006 | Heyes et al. | 604/406 |
| 2002/0107500 | A1 | | 8/2002 | Takagi | 604/406 |
| 2002/0130139 | A1 | * | 9/2002 | Shiraishi et al. | 222/105 |

FOREIGN PATENT DOCUMENTS

| | | | |
|---|---|---|---|
| EP | 1 228 776 | A1 | 8/2002 |
| EP | 0 116 362 | A2 | 8/2004 |
| GB | 2 052 948 | A | 2/1981 |
| JP | 53-32592 | | 3/1978 |
| JP | 61-80250 | U | 5/1986 |
| JP | 3-149050 | A | 6/1991 |
| JP | 3-236848 | | 10/1991 |
| JP | 7-299134 | A | 11/1995 |
| JP | 8-52196 | A | 2/1996 |
| JP | 8-141049 | A | 6/1996 |
| JP | 8-196875 | A | 8/1996 |
| JP | 8-229102 | A | 9/1996 |
| JP | 9-140770 | A | 6/1997 |
| JP | 9-173416 | A | 7/1997 |
| JP | 9-313597 | A | 12/1997 |
| JP | 10-84942 | A | 4/1998 |
| JP | 10-328269 | A | 12/1998 |
| JP | 2002-224195 | A | 8/2002 |
| WO | 96/29113 | A1 | 9/1996 |
| WO | 98/48765 | A1 | 11/1998 |
| WO | 02/072175 | A1 | 9/2002 |

* cited by examiner

LIQUID-MEDICINE INJECTION PORT DEVICE, AND LIQUID-MEDICINE CONTAINER PROVIDED WITH THE SAME

This application is a 371 of PCT/JP02/09407 filed Sep. 13, 2002, and claims priority to Japanese patent applications 2001-279182 filed Sep. 14, 2001, and 2002-231489 filed Aug. 8, 2002.

TECHNICAL FIELD

The present invention relates to a liquid-medicine injection port device, which is used for injecting and mixing liquid medicines, specifically mixing a liquid medicine into a liquid to be injected such as a transfusion solution, aseptically and simply, and a liquid-medicine container provided with the liquid-medicine injection port device.

BACKGROUND ART

Clinically, it is a matter of common practice that various medicines are simultaneously given to a patient. For example, in the case of injecting vitamins or the like into a vein, they must not be stored in a liquid-medicine container such as a transfusion-solution pack and conduct high-pressure steam sterilization processing beforehand. This is because vitamins deteriorate upon heated. When using it, therefore, it is necessary to inject and mix (referred to as injection-mix) it into a liquid-medicine container which stores another liquid medicine in advance. In short, mixing needs to be conducted in the liquid-medicine container.

If the above described liquid medicine is injection-mixed into a liquid-medicine container, conventionally, there has been used the injection-mixing method of piercing a rubber stopper of a liquid-medicine discharge port in the liquid-medicine container with an injection needle. In this method, however, it has been hard to ensure asepsis when an injection-mixing operation is conducted. If microorganisms (or germs) get mixed from the outside when the injection-mixing operation is conducted, the microorganisms propagate themselves in a mixed injection solution while the mixed injection solution is given to a patient. Especially, if an injection solution is, for example, a transfusion solution for nutrition, such as a high-calorie transfusion solution, there is a risk that microorganisms may propagate themselves while it is given, even though only a small number of microorganisms get mixed inside. Thus, there is a possibility that numerous microorganisms may be injected, together with the transfusion solution, into the body of a patient during the latter part of the time when the transfusion solution is given. If such a mixed injection solution is given, that produces some serious side effects such as septicemia and endotoxin shock on the patient. Hence, it is necessary to take the safety of a patient sufficiently into account, so that asepsis can be secured when an injection-mixing operation is conducted.

It is an object of the present invention to provide a liquid-medicine injection port device which is capable of injecting a liquid medicine aseptically and has a smaller number of component parts and a smaller and simpler structure than in any conventional ones, and a liquid-medicine container provided with this liquid-medicine injection port device.

DISCLOSURE OF THE INVENTION

A liquid-medicine injection port device according to the present invention, as the gist thereof, comprising: a liquid-medicine inlet which is formed at an upper end thereof; a liquid-medicine outlet which is formed at a lower end thereof, the liquid-medicine outlet being connected to a liquid-medicine container; a liquid passageway which connects the liquid-medicine inlet and the liquid-medicine outlet; a germ-removal filter which is provided in the liquid passageway; and a closure which closes the liquid passageway underneath the germ-removal filter and opens the liquid passageway easily.

Furthermore, in this liquid-medicine injection port device, the closure may be used which is opened by the injection pressure of a liquid medicine which is injected from the liquid-medicine inlet.

Furthermore, this closure may be a film which blocks the liquid passageway. The film has a weak part which is broken by a liquid-medicine injection pressure.

Furthermore, this closure may be a film which blocks the liquid-medicine outlet. The film is melted and attached, or is glued, to the periphery of the liquid-medicine outlet to cover the liquid-medicine outlet; and the strength of the melting-attachment or gluing is such a degree that the film is peeled by a liquid-medicine injection pressure.

Furthermore, this closure may be a cylindrical film which blocks the liquid-medicine outlet. One end of the film is fixed with kept open on the periphery of the liquid-medicine outlet to cover the liquid-medicine outlet; and the interior surfaces of the other end thereof are melted and attached, or are glued, to each other to close the other end, at such a strength that it is broken by a liquid-medicine injection pressure.

Furthermore, this closure may be an elastic member which blocks the liquid-medicine outlet. The elastic member is deformed by receiving a liquid-medicine injection pressure to open the liquid-medicine outlet.

Furthermore, this closure may be a closure member which is inserted into the liquid-medicine outlet. The closure member clings to the inside of the liquid-medicine outlet, at such a strength that it comes off the liquid-medicine outlet by a liquid-medicine injection pressure.

Furthermore, in this closure, a means may be provided which receives the closure member that comes off the liquid-medicine outlet when a liquid medicine is injected.

Furthermore, in a liquid-medicine injection port device provided with such a closure, the liquid-medicine inlet is sealed up with a rubber elastic body which is pierced with an injection needle to form a liquid-medicine storage space between the liquid-medicine inlet and the germ-removal filter; a compressor may be provided which compresses the inner volume of the liquid-medicine storage space; and the liquid-medicine injection pressure of a liquid medicine which is once injected into the liquid-medicine storage space is heightened by the compressor to compressively send the liquid medicine to the side of the germ-removal filter.

Furthermore, particularly, in this liquid-medicine injection port device, the closure may be used which is opened by a movement of a main-body member provided with the liquid-medicine inlet and the germ-removal filter.

Furthermore, in this closure, an up-and-down movement of the main-body member may allow the closure member to be moved or broken to open the closure.

Furthermore, in this closure, the main-body member may be slid up and down. The liquid-medicine outlet which is formed in a side of a hanging portion of the main-body member is blocked with a slide surface when the main-body member is in an upper position; and it is away from the slide surface and opened when it is slid downward.

Furthermore, in this closure, a turning operation of the main-body member may allow the closure member to be moved or broken to open the closure.

Furthermore, in this closure, the main-body member may be made turnable. The liquid-medicine outlet is formed in the side of a hanging portion of the main-body member; and an opening portion which leads to the outside is provided at a part of a turning-and-rubbing surface with which the liquid-medicine outlet is in contact.

Furthermore, in this closure, underneath the main-body member, an inner-lid member may be provided which engages with the main-body member so as to turn together with the main-body member. The inner-lid member is housed in the liquid passageway which is relatively widened; at least two liquid-medicine outlets are provided which are in contact with the lower surface of the inner-lid member and are away from the turning-center axis of the main-body member; and the inner-lid member has blind parts which cover the liquid-medicine outlets from the inside and has such a shape that the liquid-medicine outlets are opened by turning of the inner-lid member.

Furthermore, particularly, in this liquid-medicine injection port device, the closure may be an open-and-close valve which blocks the liquid passageway. The open-and-close valve is opened by an operation of an operation member, which penetrates the side wall of the liquid-medicine injection port device and is connected to the open-and-close valve.

Furthermore, in this closure, the open-and-close valve may be opened by turning the operation member.

Furthermore, in this closure, the open-and-close valve may be opened with a slide of the operation member, the slide crossing the liquid passageway.

Furthermore, particularly, in this liquid-medicine injection port device, the closure may be a partition wall which blocks the liquid-medicine outlet. The partition wall is broken and opened by an operation of an operation member which penetrates the side wall of the liquid-medicine injection port device.

Furthermore, a liquid-medicine container provided with the liquid-medicine injection port device according to the present invention, as the gist thereof, comprising a liquid-medicine injection port device according to any of the above described ones.

Furthermore, a liquid-medicine container provided with the liquid-medicine injection port device according to the present invention, as another gist thereof, which includes a liquid-medicine injection port device and a liquid-medicine discharge port device, is provided with two front and back sheets and is shaped like a bag, in which: an injection chamber provided with a liquid-medicine injection port device and a storage chamber storing a liquid medicine in advance are divided by a weak seal portion which is formed by melting and attaching, or gluing, the two front and back sheets to each other at such a strength that they are easily peeled.

Furthermore, particularly, this weak seal portion may be peeled by receiving the injection pressure of a liquid medicine which is injected from the liquid-medicine injection port device to allow the injection chamber to lead to the storage chamber.

Particularly, a projection may be formed in either or both of the front and back surfaces of this weak seal portion. The projection is picked up and pulled so that the weak seal portion is peeled and separated into the two front and back sheets.

BRIEF DESCRIPTION OF THE DRAWINGS

FIG. 3 shows details of an outlet member shown in FIG. 1, according to the present invention.

FIG. 4 illustrates the shape of a weak part which is formed in a closure film shown in FIG. 1, according to the present invention.

FIG. 5 shows another liquid-medicine injection port device according to the present invention.

FIG. 8 shows still another liquid-medicine injection port device according to the present invention.

FIG. 9 shows the liquid-medicine outlet and its vicinity according to the present invention.

FIG. 11 shows still another liquid-medicine injection port device according to the present invention.

FIG. 19 shows still another liquid-medicine injection port device according to the present invention; FIG. 19B showing a state in which a liquid-medicine outlet is closed; and FIG. 19C showing a state in which the liquid-medicine outlet is opened.

BEST MODE FOR CARRYING OUT THE INVENTION

Next, embodiments of a liquid-medicine injection port device and a liquid-medicine container according to the present invention will be described in detail with reference to drawings.

Figure 1:
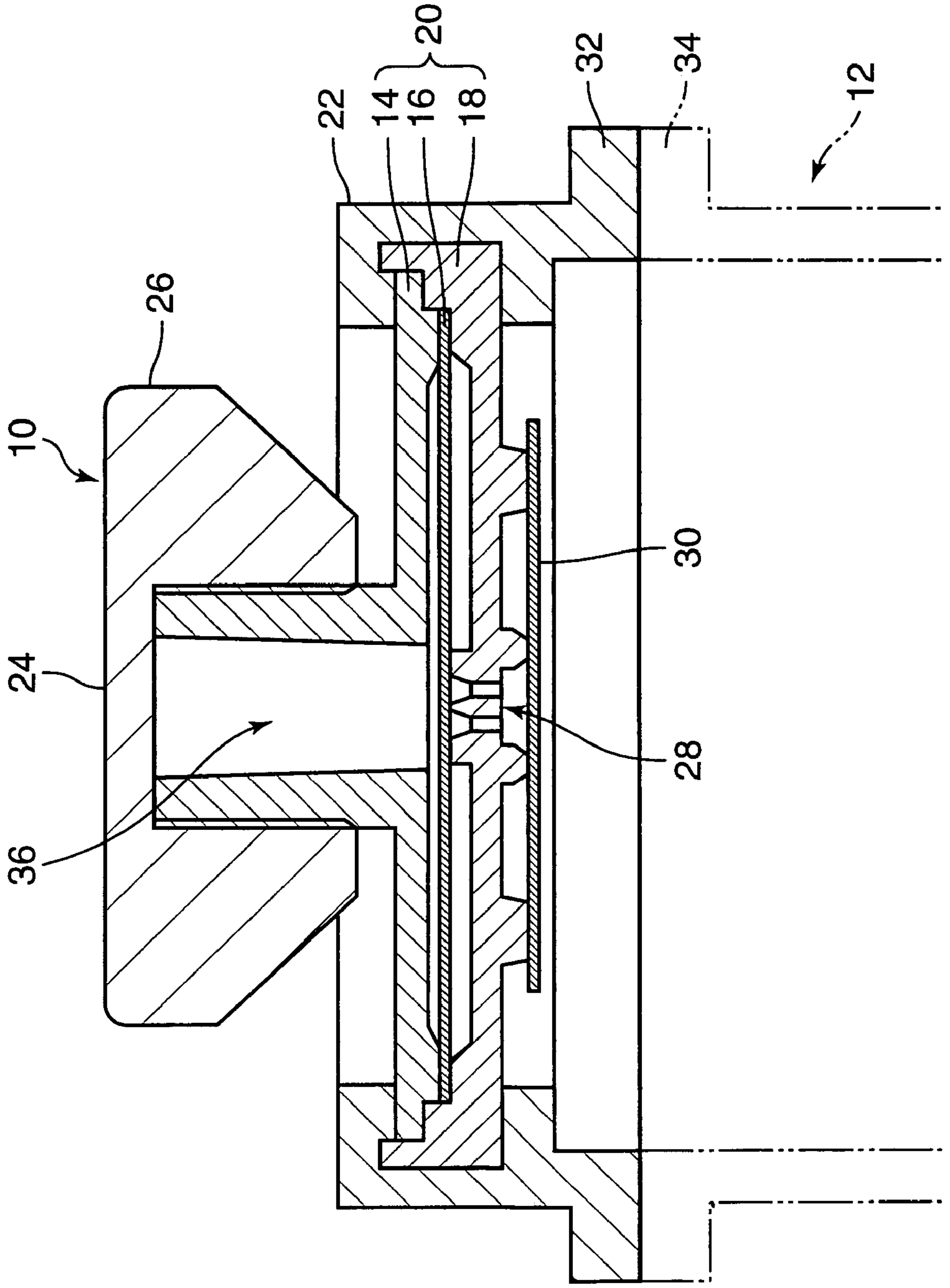
FIG. 1 is a longitudinal sectional view of a liquid-medicine injection port device according to the present invention.
Figure 2:
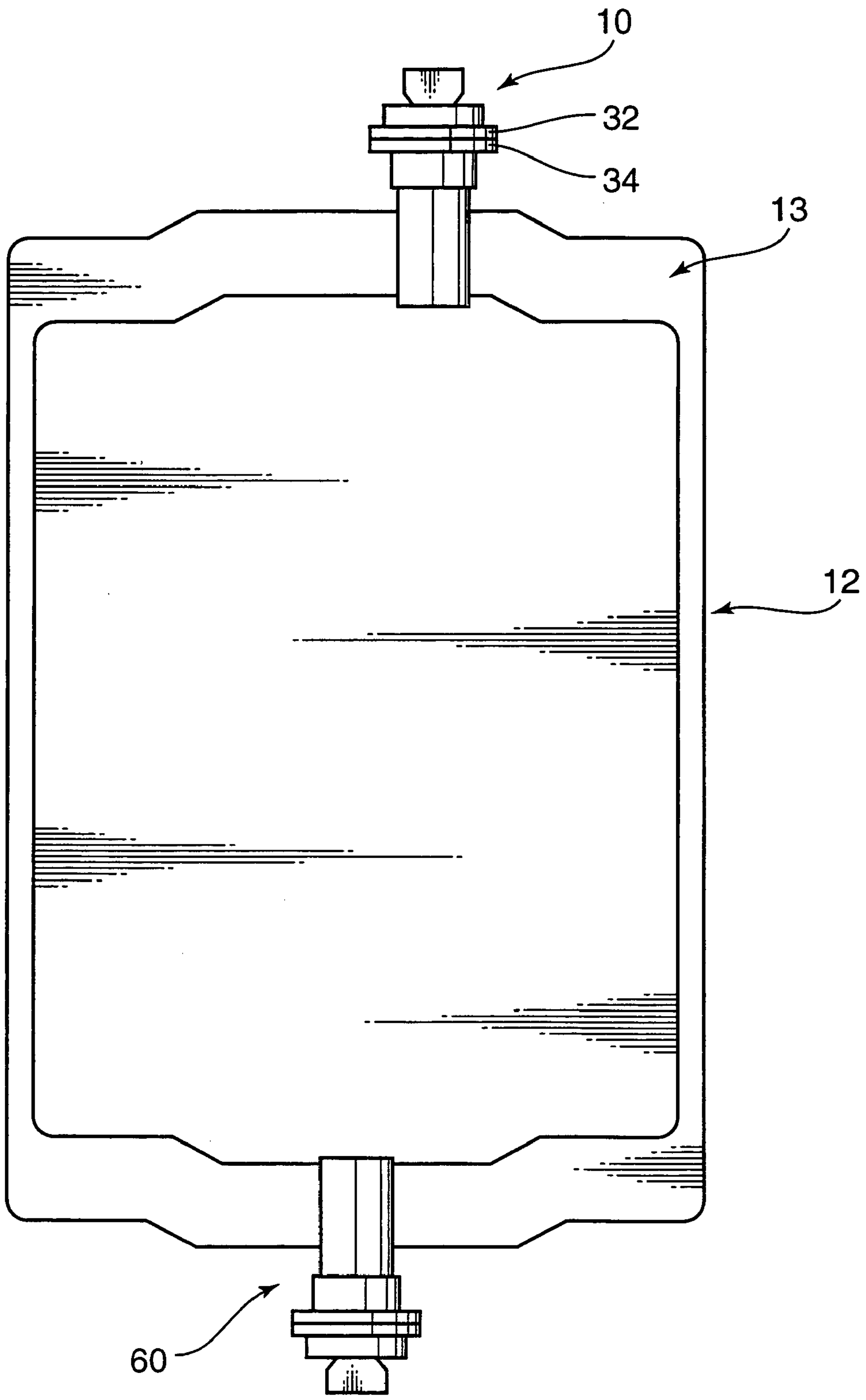
FIG. 2 is a front view of a liquid-medicine container according to the present invention.

FIG. 1 shows a preferred liquid-medicine injection port device 10 embodying the present invention. FIG. 2 shows a liquid-medicine container (or a transfusion-solution pack) 12 which the liquid-medicine injection port device 10 is attached to. The liquid-medicine injection port device 10 is configured by: a main-body member 20 which is formed by placing an inlet member 14, a germ-removal filter 16 and an outlet member 18 on top of one another in that order; a cylindrical member 22 which the side part of the main-body member 20 is held in; a cap 26 which covers a liquid-medicine inlet 24 formed in the upper end of the inlet member 14 and is attachable thereto, and detachable therefrom; and a closure film 30 which blocks a liquid-medicine outlet 28 formed in the central lower part of the outlet member 18. A flange 32 formed at the lower end of the cylindrical member 22 is melted and attached to a flange 34 formed at the upper end of the liquid-medicine container 12, so that the liquid-medicine injection port device 10 is fixed on the upper part of the liquid-medicine container 12. A liquid passageway 36 is formed which leads from the liquid-medicine inlet 24, through the inlet member 14, the germ-removal filter 16 and the outlet member 18, to the liquid-medicine outlet 28.

Figure 3A:
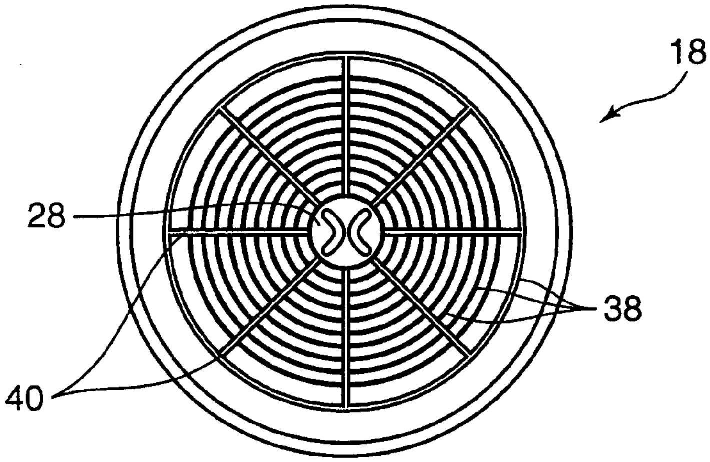
FIG. 3A being a top view.
Figure 3B:
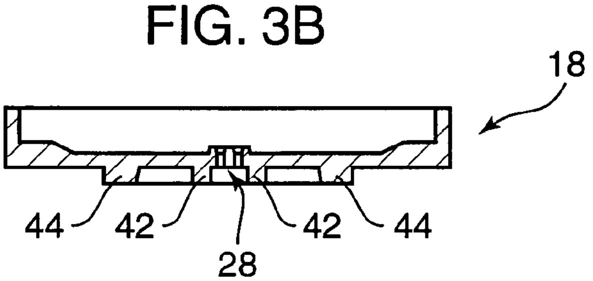
FIG. 3B being a longitudinal sectional view.
Figure 3C:
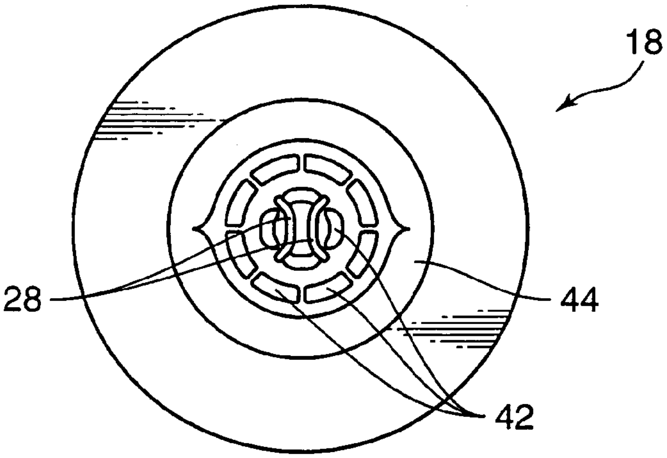
FIG. 3C being a bottom view.

In the liquid-medicine injection port device 10 according to the present invention, the upside means the side on which the liquid-medicine inlet 24 is provided, and the downside means the side on which the liquid-medicine outlet 28 is provided in the direction where it is connected to the liquid-medicine container 12. The liquid-medicine inlet 24 is shaped so as to be connected to a syringe which stores a liquid medicine to be injection-mixed, and it is gently tapered off downward. The germ-removal filter 16 is disposed with its front surface wide open, so that a liquid medicine can be filtrated over an area as large as possible. As shown in FIG. 3, in the upper surface of the outlet member 18 are formed circular grooves 38 and radial grooves 40 in great numbers. This allows the liquid medicine which has passed through the germ-removal filter 16 to flow toward the liquid-medicine outlet 28 formed in its central part and to converge in it.

In the lower surface of the outlet member 18, there are formed twelve projections 42 which doubly surround the liquid-medicine outlet 28, and in addition, a circular projection 44 which surrounds them. The closure film 30 is melted and attached to the circular projection 44 to block the liquid-medicine outlet 28. The twelve projections 42 have the function of supporting the closure film 30 against the pressure applied on the closure film 30 from behind. The projections 42 are suitably away from each other, so that a liquid medicine can move freely between these projections 42.

Figure 4A:
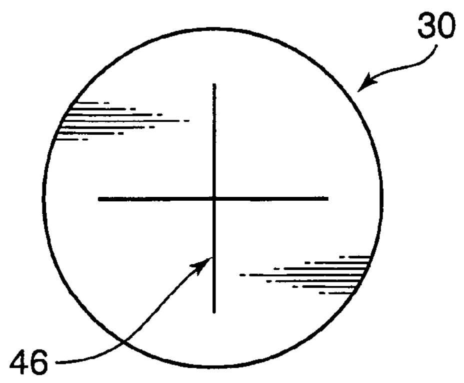
FIG. 4A showing the shape of a cross.

In the closure film 30 is formed a weak part which is broken by a liquid-medicine injection pressure. The weak part is formed with scratches engraved by a Thomson blade, a heat press or the like, perforations, or the like. For example, a weak part 46 shown in FIG. 4A is a cross-engraved scratch. It usually closes the liquid-medicine outlet 28, and does not break even though coming into contact with a liquid medicine in the liquid-medicine container 12. This prevents it from going into the liquid-medicine injection port device 10. If injection-mixing is conducted from the liquid-medicine inlet 24, the weak part 46 receives the injection pressure of the injection-mixed liquid medicine through the liquid-medicine outlet 28. Then, this thin scratch is broken and opened downward, and thus, the closed liquid passageway 36 is opened and leads to the inside of the liquid-medicine container 12.

Figure 4B:
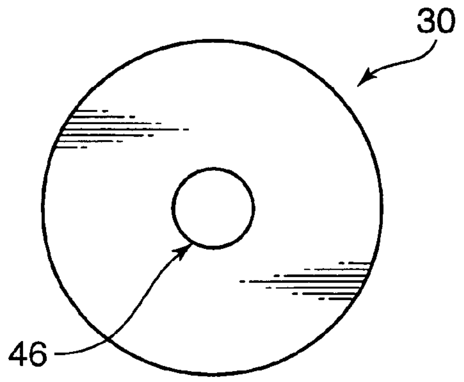
FIG. 4B showing the shape of a circle.
Figure 4C:
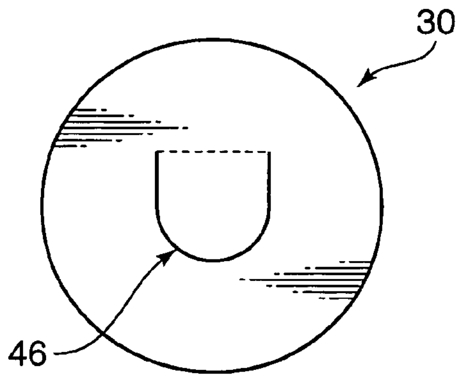
FIG. 4C showing the shape of a tongue.

In the closure film 30 shown in FIG. 4B is formed the weak part 46 which is a circular scratch. If it receives a liquid-medicine injection pressure, then its circular hole is designed to open. In the closure film 30 shown in FIG. 4C is formed the U-shaped weak part 46, and its opening part would be formed which hangs down like a tongue. However, the shape of the weak part 46 is not limited to these illustrations. It is most suitably designed according to the property and state of an injection-mixed liquid medicine, injection-mixing pressure, or the like.

With respect to the liquid-medicine injection port device 10 according to the present invention which has such a structure as described above, as shown in FIG. 2, when it is attached to the liquid-medicine container 12, a liquid medicine is injected from the liquid-medicine inlet 24 before the closure film 30 is broken. Thus, the liquid passageway 36 leads to the liquid-medicine container 12. This prevents the liquid medicine stored in the liquid-medicine container 12 from going into the liquid-medicine injection port device 10, at least before it is used (or before an injection-mixing operation is conducted). In addition, with the liquid-medicine injection port device 10 kept attached, the liquid medicine stored in the liquid-medicine container 12 is aseptically held. Besides, injection-mixing can be easily conducted without doing any other special work. All you have to do is to take off the cap 26 and inject a liquid medicine from the liquid-medicine inlet 24.

As the germ-removal filter 16, especially, limitations are not necessarily placed, but each type of filter usually used in the art may be suitably used, for example, a membrane type, a screen type, a depth type, an anisotropic type, or the like. Among them, the membrane-type filter is especially preferable. If the germ-removal filter 16 is realized with the membrane-type, its hole diameter (or mesh fineness) should preferably be chosen to be 0.01 μm to 1.0 μm, so that it can cut off the passage of germs. More preferably, it should be chosen 0.01 μm to 0.5 μm. In addition, as a material forming the germ-removal filter 16, there are enumerated cellulose acetate, regenerated cellulose, cellulose ester, nylon, polytetrafluoroethylene, polystyrene, polycarbonate, acrylic-system resin, polyolefin, polyvinylidene difluoride, polyether sulfone, and the like. However, it is not limited to these.

The material of the inlet member 14, the outlet member 18, the cylindrical member 22, the cap 26 and the like, is not limited especially. However, plastics having superior moldability are used preferably. Above all, it is especially preferable that materials having great chemical-resistance to a liquid medicine to be injection-mixed, great heat-resistance to high-pressure steam sterilization, superior melting-and-attaching properties useful for the connection between each member or their connection to the liquid-medicine container 12, and the like, are used, such as polyethylene, polypropylene, polyvinyl chloride, polyester, polycarbonate, and the like. Preferably, the outlet member 18 should be the same material as the liquid-medicine container 12, so that they can be easily connected by melting attachment.

In addition, the closure film 30 is not especially limited, as long as it has chemical-resistance and a suitable thickness for forming the weak part 46. Preferably, it should be melted and attached to the circular projection 44. To do this, it is preferable that a film is used which is made of the same material as the outlet member 18, or a material blended with the material of the outlet member 18. For example, if the outlet member 18 is made of polyethylene, then polyethylene, a polymer blend of polyethylene and polypropylene, or the like, is used preferably. However, a film which is difficult to melt and attach to the outlet member 18 may also be used and glued to the circular projection 44 to close the liquid-medicine outlet 28.

The liquid-medicine container 12 provided with the liquid-medicine injection port device 10 according to the present invention is sterilized in advance before it is used (or injection-mixing is conducted). Specifically, with storing a liquid medicine in the liquid-medicine container 12, it undergoes processing, such as high-pressure steam sterilization, ethylene-oxide gas sterilization, and γ-ray sterilization. Then, it is sealed with the cap 26 to be kept aseptic. When injection-mixing is conducted, first, the cap 26 is removed, and then, using a syringe or an injection needle, a liquid medicine is injected from the liquid-medicine inlet 24. The germs which have got mixed into the injected liquid medicine are hindered from passing through the germ-removal filter 16, and thus, stop short of the inside of the liquid-medicine container 12. Therefore, the injection-mixed injection solution remains aseptic, allowing it to be safely given to a patient.

Figure 5A:
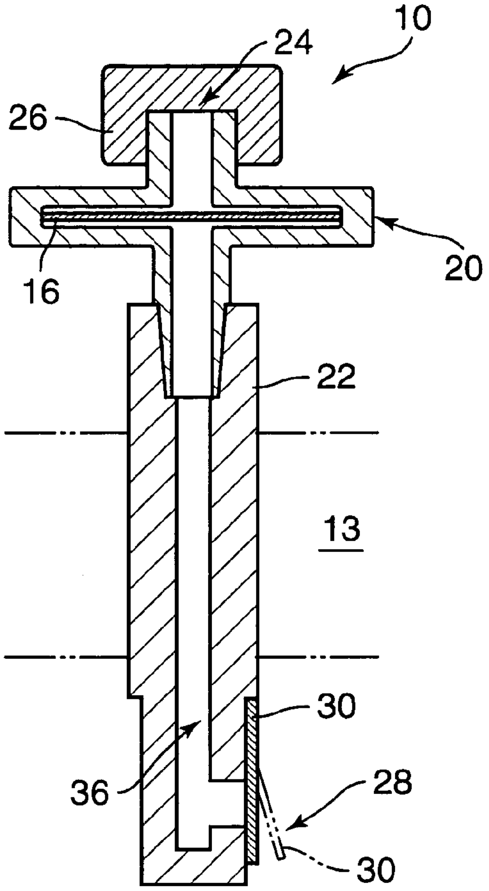
FIG. 5A being a longitudinal sectional view.
Figure 5B:
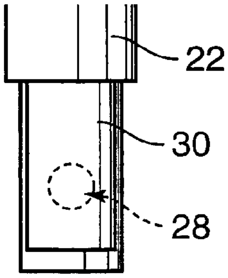
FIG. 5B being a front view of a liquid-medicine outlet and its vicinity.

A closure in the liquid-medicine injection port device 10 shown in FIG. 5 is the closure film 30 blocking the liquid-medicine outlet 28. The liquid-medicine injection port device 10 is configured by: the main-body member 20 which is a so-called top-shaped filter including the liquid-medicine inlet 24 and the germ-removal filter 16; the cylindrical member 22 connected to the lower part of the main-body member 20; and the cap 26 covering the liquid-medicine inlet 24. The cylindrical member 22 is inserted into the liquid-medicine container 12. Then, it is melted and attached, or glued, to an edge portion 13 of the liquid-medicine container 12 (omitted in the figure). Thereby, it is fixed airtight thereto.

In this liquid-medicine injection port device 10, the liquid-medicine outlet 28 is formed in the lowermost side wall of the cylindrical member 22 and is blocked with the closure film 30. The closure film 30 is melted and attached, or glued, to the periphery of the liquid-medicine outlet 28. The strength of the melting-attachment or gluing is such a degree that it is peeled by a liquid-medicine injection pressure applied when a liquid medicine has been injected from the liquid-medicine inlet 24. Thus, before it is used, the liquid-medicine outlet 28 is blocked with the closure film 30, thereby preventing a liquid medicine in the liquid-medicine container 12 from going into the liquid-medicine injection port device 10. If injection-mixing is conducted, the closure film 30 is peeled to open the liquid-medicine outlet 28 automatically. Then, the injected liquid medicine goes into the liquid-medicine container 12 and is mixed with a liquid medicine already stored in the liquid-medicine container 12.

Figure 6:
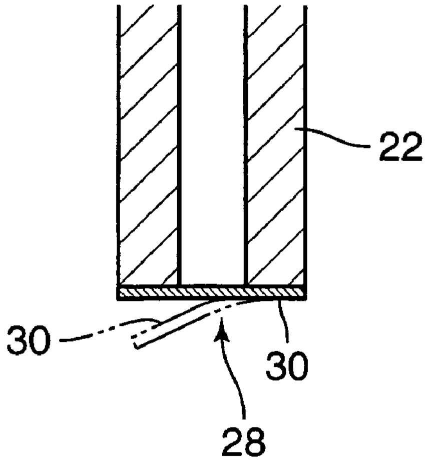
FIG. 6 is a longitudinal sectional view of the liquid-medicine outlet and its vicinity according to the present invention.

According to this embodiment in which the liquid-medicine outlet 28 is blocked with the film at such a strength that it is peeled by a liquid-medicine injection pressure, the location or shape of the liquid-medicine outlet 28 is not limited especially. FIG. 6 shows an example in which the liquid-medicine outlet 28 is formed in the bottom of the cylindrical member 22. Alternatively, using a configuration similar to that shown in FIG. 1, the strength at which the closure film 30 is fixed on the outlet member 18 may also be suitably controlled so that it can be easily peeled. Preferably, a part of the peeled closure film 30 should remain attached so that it will not fall into the liquid-medicine container 12.

Figure 7:
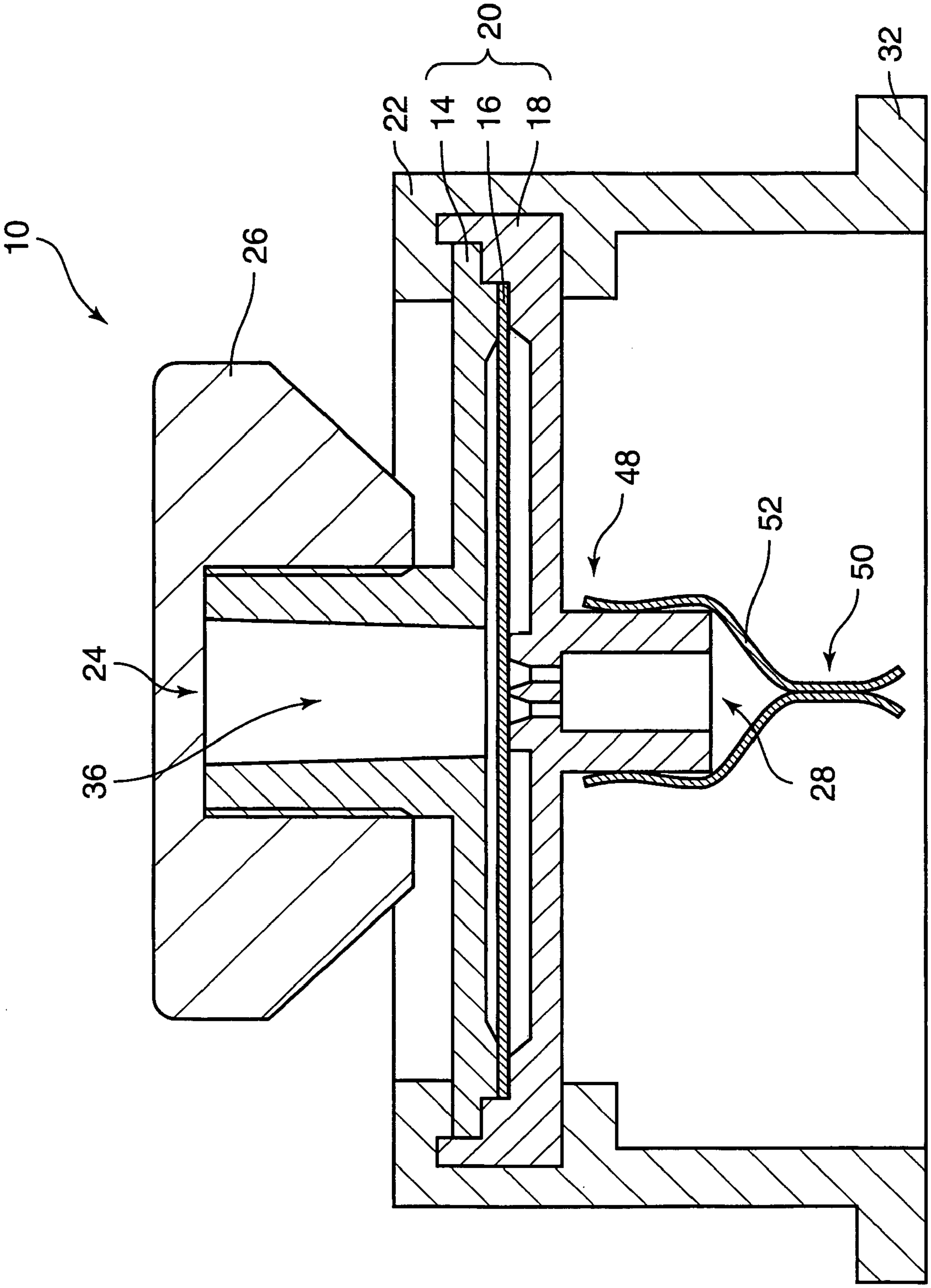
FIG. 7 is a longitudinal sectional view of another liquid-medicine injection port device according to the present invention.

The liquid-medicine injection port device 10 shown in FIG. 7 shows another preferred embodiment according to the present invention. As the closure of blocking the liquid passageway 36 is used a cylindrical film, and one of its ends is closed. Specifically, an opened end 48 of a cylindrical film 52 is fixed on the periphery of the liquid-medicine outlet 28 to cover the liquid-medicine outlet 28. The interior surfaces of its other end 50 are melted and attached to each other to close it, at such a strength that it is broken by a liquid-medicine injection pressure. Therefore, when a liquid medicine has been injected from the liquid-medicine inlet 24, the closed end 50 of the cylindrical film 52 is opened by the liquid-medicine injection pressure. Thus, the injected liquid medicine goes into the liquid-medicine container 12 (refer to FIG. 2). The means of fixing the opened end 48 of the cylindrical film 52 on the periphery of the liquid-medicine outlet 28 is not limited, but melting attachment, gluing, banding or the like, is preferable. The interior surfaces of the other end 50 may be melted and attached to each other. However, their melting attachment may also be conducted by placing a different kind of film between them. Herein, the film which blocks the liquid passageway 36 may also be disposed in the liquid passageway 36.

Figure 8A:
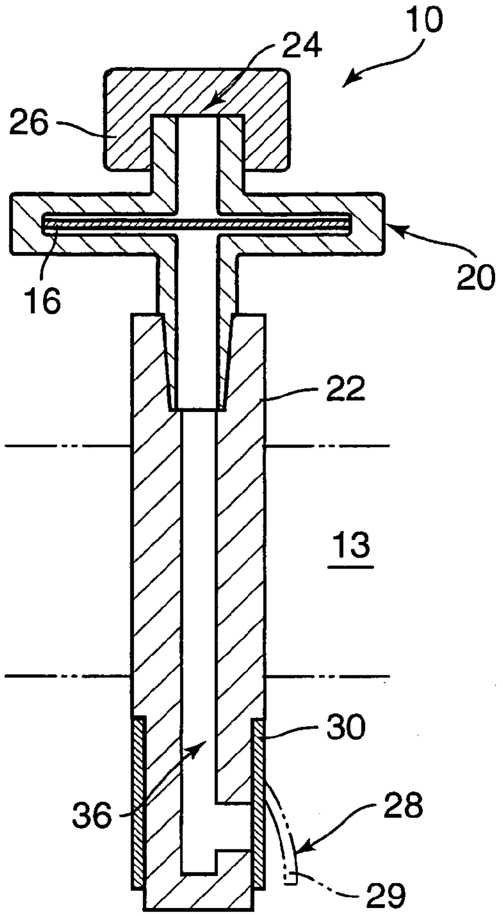
FIG. 8A being a longitudinal sectional view.
Figure 8B:
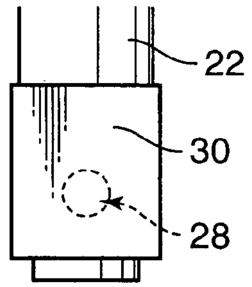
FIG. 8B being a front view of a liquid-medicine outlet and its vicinity.

FIG. 8 shows an example in which the closure is an elastic member which blocks the liquid-medicine outlet 28. The liquid-medicine outlet 28 formed in the lowermost side of the cylindrical member 22 is covered with a tube 29 which is a rubber elastic body. This prevents a liquid medicine in the liquid-medicine container 12 from going into the liquid-medicine injection port device 10. When a liquid medicine for injection-mixing is injected from the liquid-medicine inlet 24, the tube 29 is swelled by the injection pressure. This creates a gap between it and the cylindrical member 22 and opens the liquid-medicine outlet 28. After the injection has stopped, the tube 29 returns to its initial position again and blocks the liquid-medicine outlet 28. In other words, the tube 29 functions as a check valve.

Figure 9A:
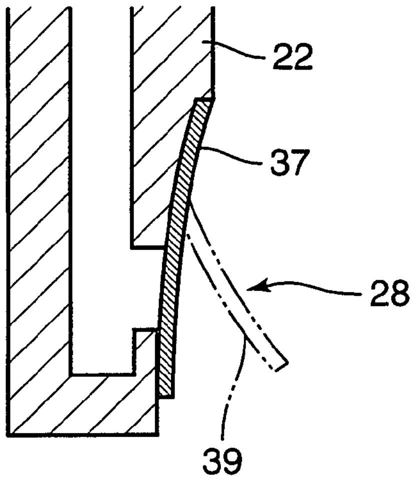
FIG. 9A being a longitudinal sectional view.
Figure 9B:
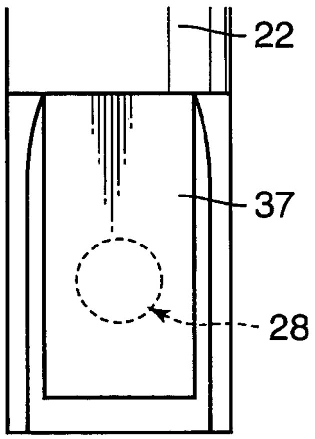
FIG. 9B being a front view.

In another example shown in FIG. 9, a plate spring 37 is used as the elastic member which blocks the liquid-medicine outlet 28. The plate spring 37 is warped by receiving a liquid-medicine injection pressure. This creates a gap between it and the cylindrical member 22 and opens the liquid-medicine outlet 28.

Figure 10:
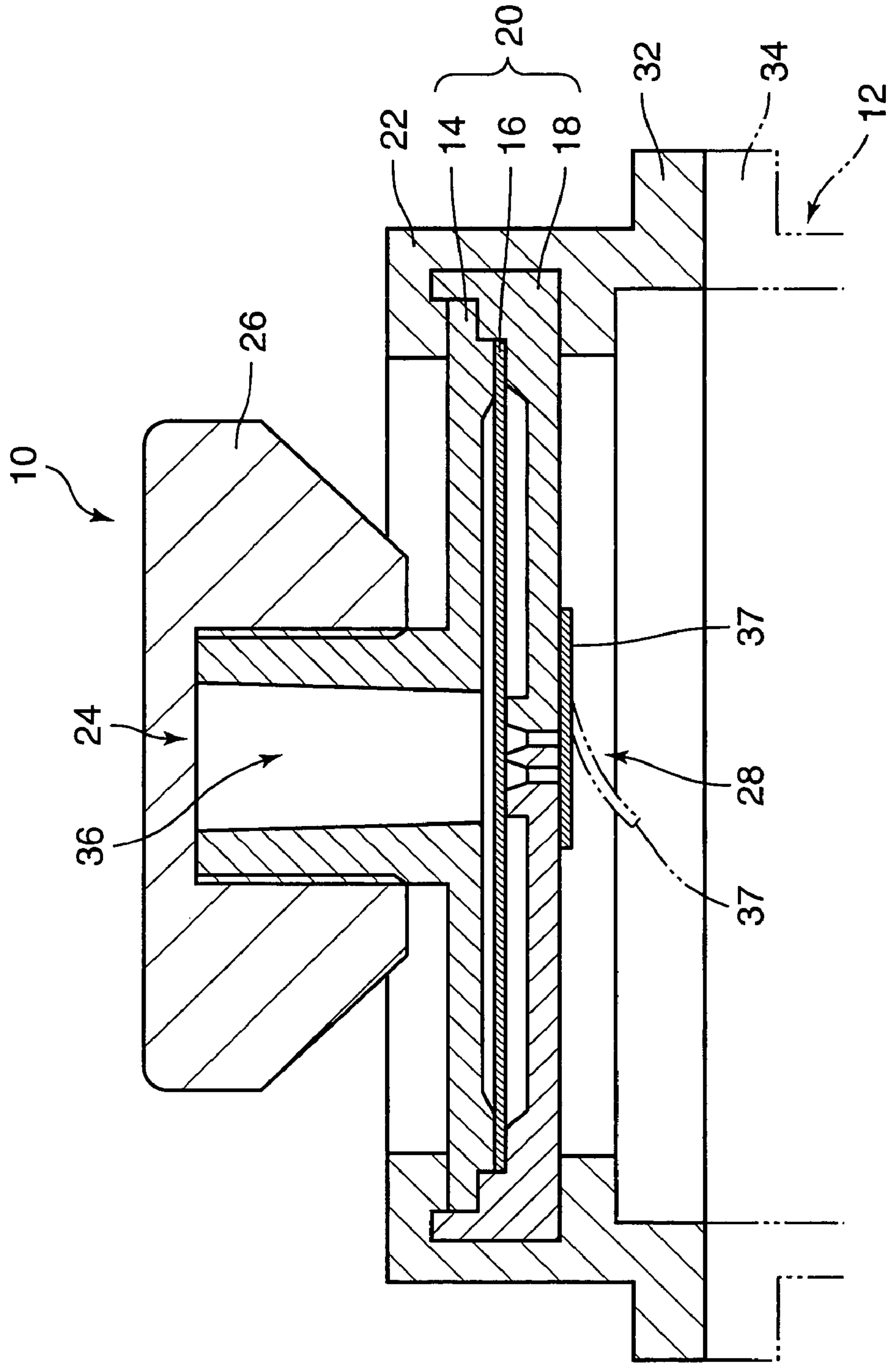
FIG. 10 is a longitudinal sectional view of still another liquid-medicine injection port device according to the present invention.

The liquid-medicine injection port device 10 shown in FIG. 10 is similar to the liquid-medicine injection port device 10 shown in FIG. 1, but the closure film 30 which blocks the liquid-medicine outlet 28 is replaced with the plate spring 37 used as the elastic member. However, the elastic member is not limited to the above described illustration. A coiled spring or the like may also be used.

Figure 11A:
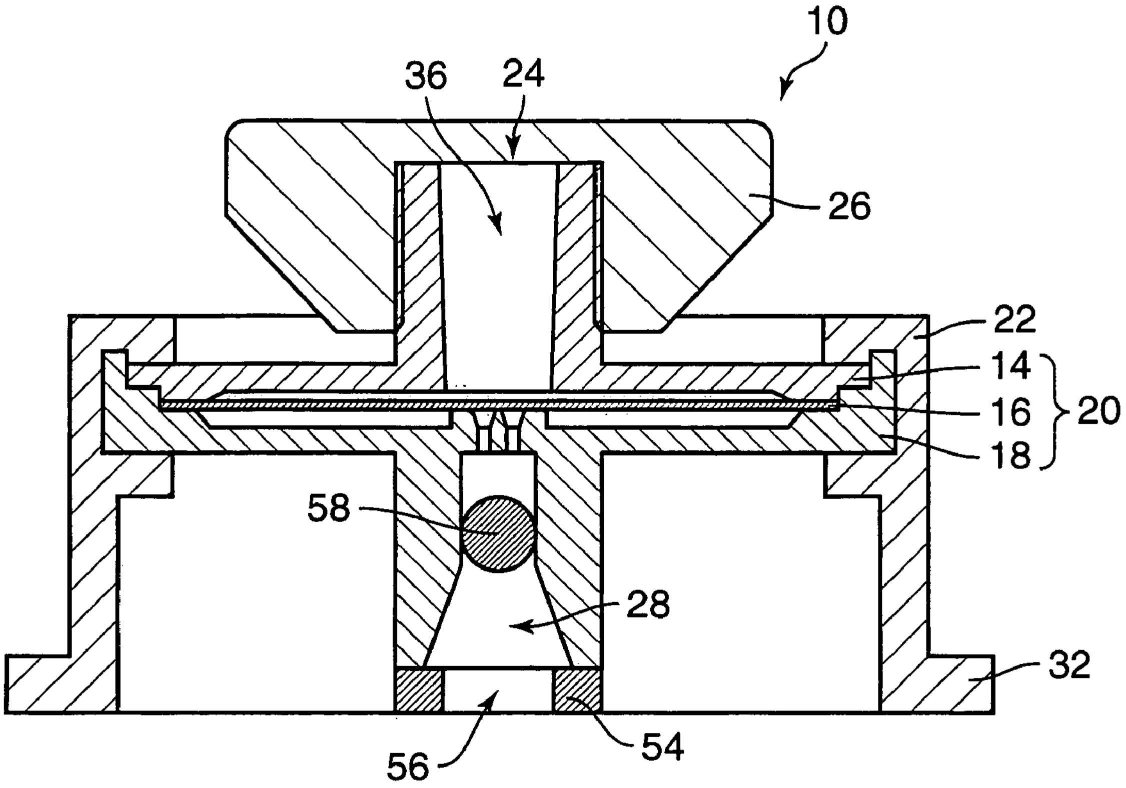
FIG. 11A being a longitudinal sectional view of the whole injection port device.
Figure 11B:
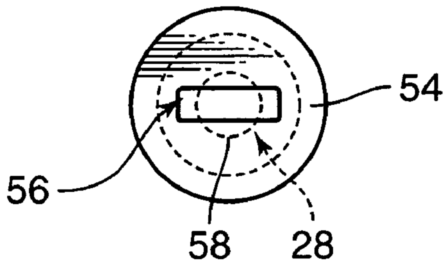
FIG. 11B being a bottom view of a capture member and its vicinity.

In the liquid-medicine injection port device 10 shown in FIG. 11, as the means of blocking the liquid passageway 36 is used a closure member 58 which is inserted into the liquid-medicine outlet 28. Specifically, the liquid-medicine outlet 28 is blocked by inserting the substantially-spherical closure member 58 into the liquid-medicine outlet 28 having a circular cross section. The closure member 58 clings to the inside of the liquid-medicine outlet 28, at such a strength that it comes off the liquid-medicine outlet 28 by a liquid-medicine injection pressure. Therefore, when a liquid medicine has been injected from the liquid-medicine inlet 24, the closure member 58 comes off and is released from the liquid-medicine outlet 28 by the liquid-medicine injection pressure. Thus, the liquid passageway 36 is opened. The shape of the closure member 58 is suitably selected in line with the shape of the liquid-medicine outlet 28. Specifically, for the circular cross-section liquid-medicine outlet 28, it should suitably be spherical, cylindrical, bottomed conical, or the like. Besides, it is preferable that the liquid-medicine outlet 28 has a proper degree of elasticity.

In this example, a receiving member 54 is attached to the bottom of the liquid-medicine outlet 28. It receives the closure member 58 which comes off and is released by the liquid-medicine injection pressure, thereby preventing it from falling into the liquid-medicine container 12 (refer to FIG. 2). This is aimed at evading occurrence of some trouble, such as the blockage of the inlet of a liquid-medicine discharge port device 60 (refer to FIG. 2) in the liquid-medicine container 12 with the fallen closure member 58. In the receiving member 54, an opening portion 56 is formed which has a substantially-rectangular shape that is narrower than the closure member 58. This allows a liquid medicine to pass through both its sides, even though it receives the closure member 58.

Figure 12:
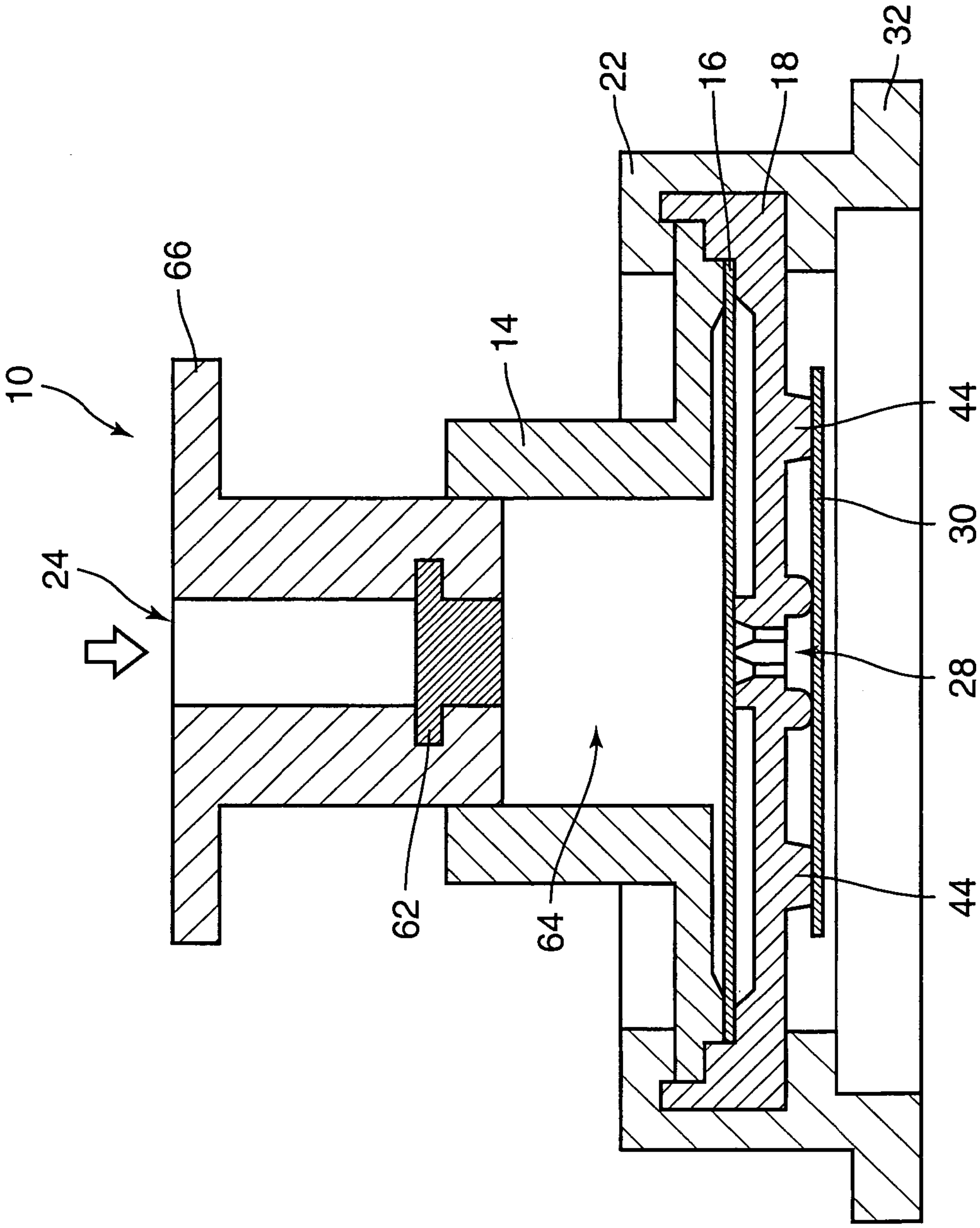
FIG. 12 is a longitudinal sectional view of still another liquid-medicine injection port device according to the present invention.

In the liquid-medicine injection port device 10 shown in FIG. 12, a compressor is provided which heightens a liquid-medicine injection pressure secondarily. A slide member 66 is disposed which can slide along the upper cylindrical interior-surface of the inlet member 14. The liquid-medicine inlet 24 formed in this slide member 66 is sealed up with a stopper body 62 which is formed with a rubber elastic body and that can be pierced with an injection needle. Between the stopper body 62 and the germ-removal filter 16 is formed a liquid-medicine storage space 64. When injection-mixing is conducted, using the injection needle which pierces the stopper body 62, a liquid medicine is first injected into the liquid-medicine storage space 64. Next, the liquid-medicine storage space 64 is compressed by moving down the slide member 66. Since the side of the liquid-medicine inlet 24 is sealed up, the liquid medicine once stored in the liquid-medicine storage space 64 receives the compression pressure strongly and flows onto the side of the germ-removal filter 16. Then, the strong compression pressure is transmitted to a closure provided underneath the germ-removal filter 16 to open the closure. The closure in this example is the closure film 30 which blocks the liquid-medicine outlet 28. The closure film 30 which is melted and attached to the circular projection 44 of the outlet member 18 receives the liquid-medicine injection pressure and is peeled. Herein, an interlock mechanism may also be provided which prevents the slide member 66 from moving down before the liquid-medicine injection port device 10 is used.

If it is used in the liquid-medicine injection port device 10 provided with a closure which is opened by a liquid-medicine injection pressure, this contrivance for heightening the liquid-medicine injection pressure secondarily helps open the closure more certainly. This is especially effective in the case where a liquid medicine is injected using an injection needle under relatively-low injection pressure. As the closure used together, any one may be used, as long as it is opened by a liquid-medicine injection pressure. It includes the closure already described using FIG. 1 to FIG. 11 or the like, in short, it is not especially limited.

Figure 13:
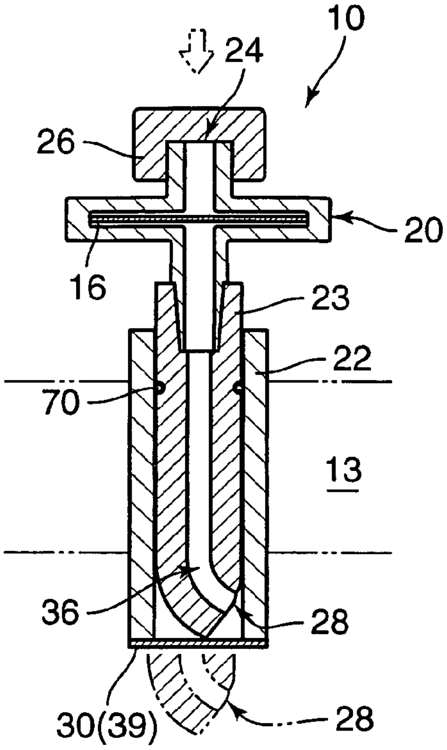
FIG. 13 is a longitudinal sectional view of still another liquid-medicine injection port device according to the present invention.
Figure 14:
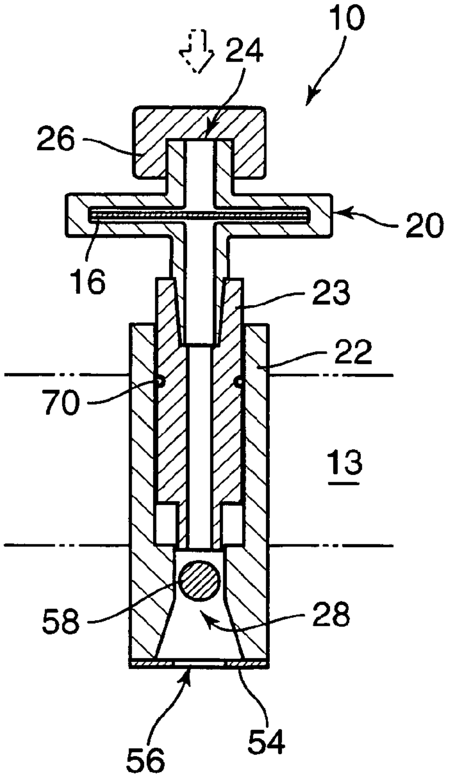
FIG. 14 is a longitudinal sectional view of still another liquid-medicine injection port device according to the present invention.

FIG. 13 and FIG. 14 show examples in which the main-body member 20 including the liquid-medicine inlet 24 and the germ-removal filter 16 moves up and down, thereby moving or breaking a closure to open the closure. Specifically, the liquid-medicine injection port device 10 shown in FIG. 13 is an example which has the function of breaking the closure. The main-body member 20 and a slide member 23 can move up and down together in the cylindrical member 22. In the slide member 23, the liquid-medicine outlet 28 is formed near its pointed end, as if it were a rocket needle. An opening portion 39 formed at the bottom of the cylindrical member 22 is blocked with the closure film 30. Therefore, if the cap 26 covering the main-body member 20 is pushed down, the slide member 23 moves down together with the main-body member 20. Then, its pointed end breaks through the closure film 30, allowing the liquid passageway 36 to lead to the liquid-medicine container 12.

The liquid-medicine injection port device 10 shown in FIG. 14 has the function of moving the closure. In this liquid-medicine injection port device 10, in the same way as the liquid-medicine injection port device 10 shown in FIG. 11, the liquid-medicine outlet 28 is blocked by inserting the substantially-spherical closure member 58 into the liquid-medicine outlet 28 having a circular cross section. Since the liquid-medicine outlet 28 is formed at the bottom of the cylindrical member 22, if the cap 26 is pushed down and the slide member 23 is moved down to get her with the main-body member 20, then the lower end of the slide member 23 hits on the closure member 58. Thus, it is pushed out of the liquid-medicine outlet 28, allowing the liquid passageway 36 to lead to the liquid-medicine container 12.

Figure 15:
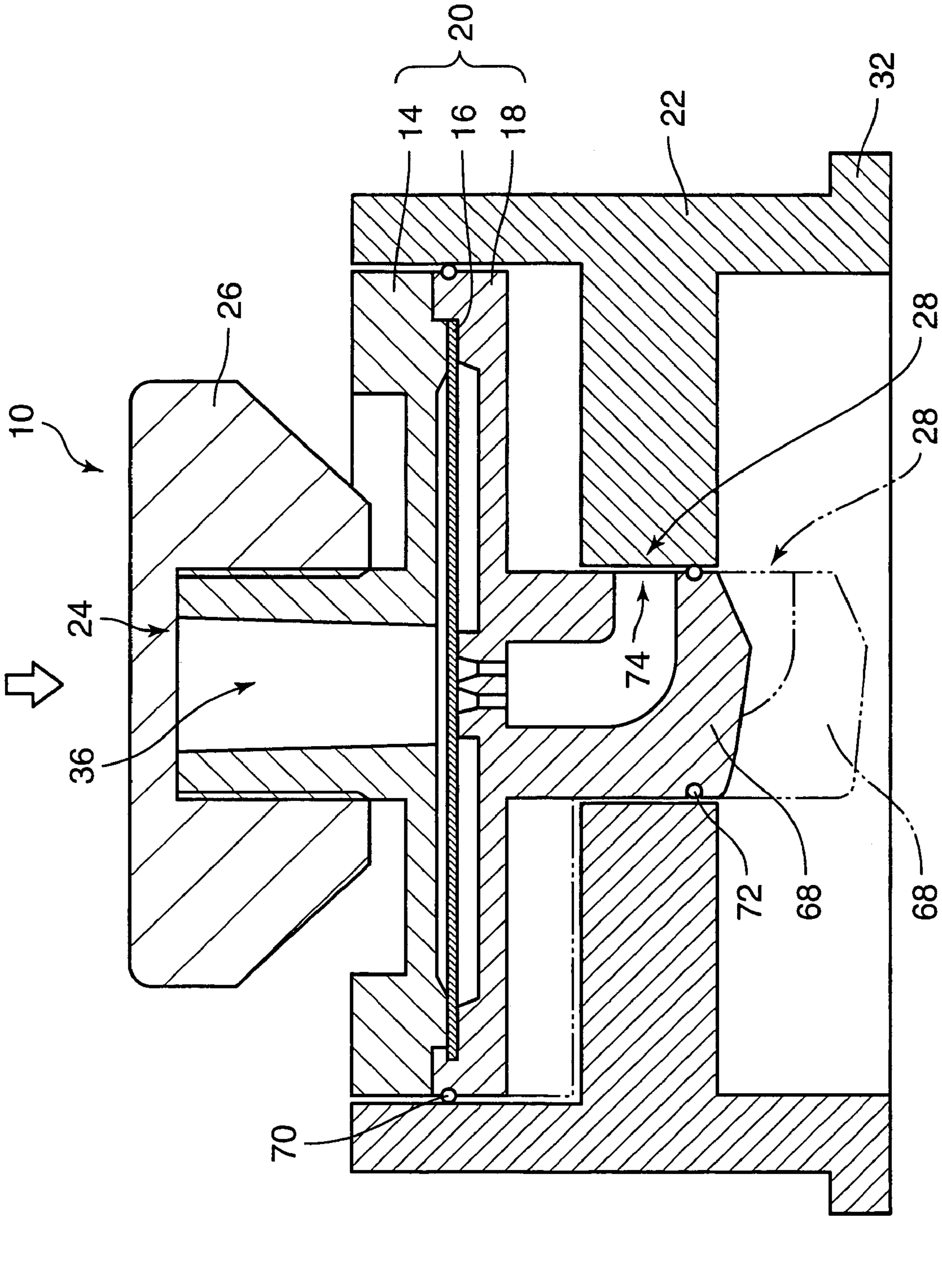
FIG. 15 is a longitudinal sectional view of still another liquid-medicine injection port device according to the present invention.
Figure 16:
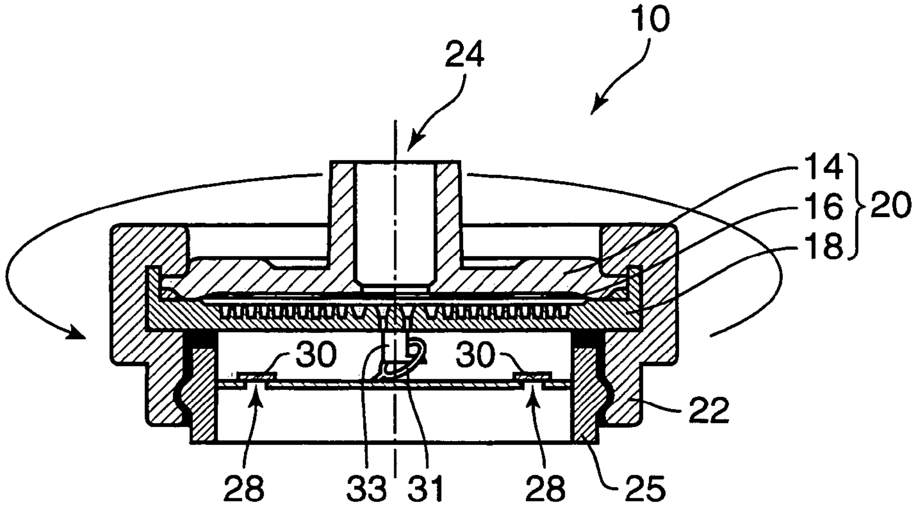
FIG. 16 is a longitudinal sectional view of still another liquid-medicine injection port device according to the present invention.

In the liquid-medicine injection port device 10 shown in FIG. 15, the main-body member 20 formed by the inlet member 14, the germ-removal filter 16 and the outlet member 18 can slide up and down along the interior surface of the cylindrical member 22. The liquid-medicine outlet 28 formed in the side of a hanging portion 68 of the outlet member 18 is blocked with a slide surface 74 when the main-body member 20 is in an upper position. On the other hand, it is away from the slide surface 74 and is opened when it has been slid downward. Before it is used (or injection-mixing is conducted), the liquid-medicine outlet 28 is kept closed. This prevents the liquid medicine stored in the liquid-medicine container 12 (refer to FIG. 2) from going into the liquid-medicine injection port device 10. Injection-mixing is conducted by moving down the main-body member 20, removing the cap 26 and injecting the liquid medicine from the liquid-medicine inlet 24. Herein, an interlock mechanism may also be provided which prevents the main-body member 20 from moving down before it is used.

Figure 17:
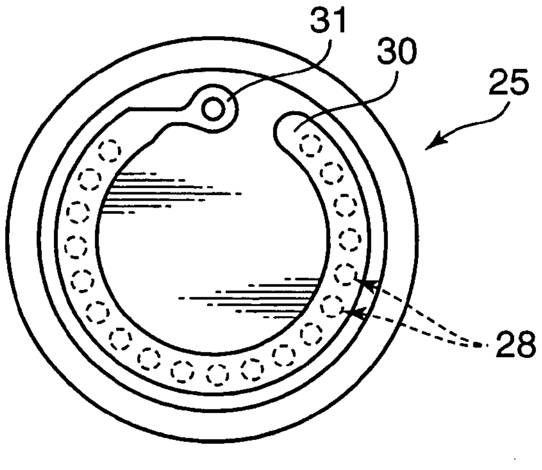
FIG. 17 is a top view of an outlet member of the liquid-medicine injection port device shown in FIG. 16, according to the present invention.

The liquid-medicine injection port device 10 shown in each of FIG. 16, FIG. 18, FIG. 19 and FIG. 20 has the function of opening the closure by turning the main-body member 20. In the liquid-medicine injection port device 10 shown in FIG. 16, the main-body member 20 and the cylindrical member 22 can turn together around an outlet member 25 to be connected to the liquid-medicine container 12 (omitted in the figure). In the outlet member 25, a large number of holes 28 are formed as a liquid-medicine outlet, and are covered and blocked from above with the horseshoe closure film 30 (refer to FIG. 17). A ring 31 formed at an end of the closure film 30 is hooked on a claw 33 for hanging. The claw 33 is formed at the bottom of the main-body member 20 and extends from its center to periphery. Hence, if the main-body member 20 and the cylindrical member 22 are turned in the direction of an arrow, the claw 33 turns with hooking the ring 31. Thus, the closure film 30 is gradually wound from the side of the ring 31 to open the liquid-medicine outlet 28.

Figure 18:
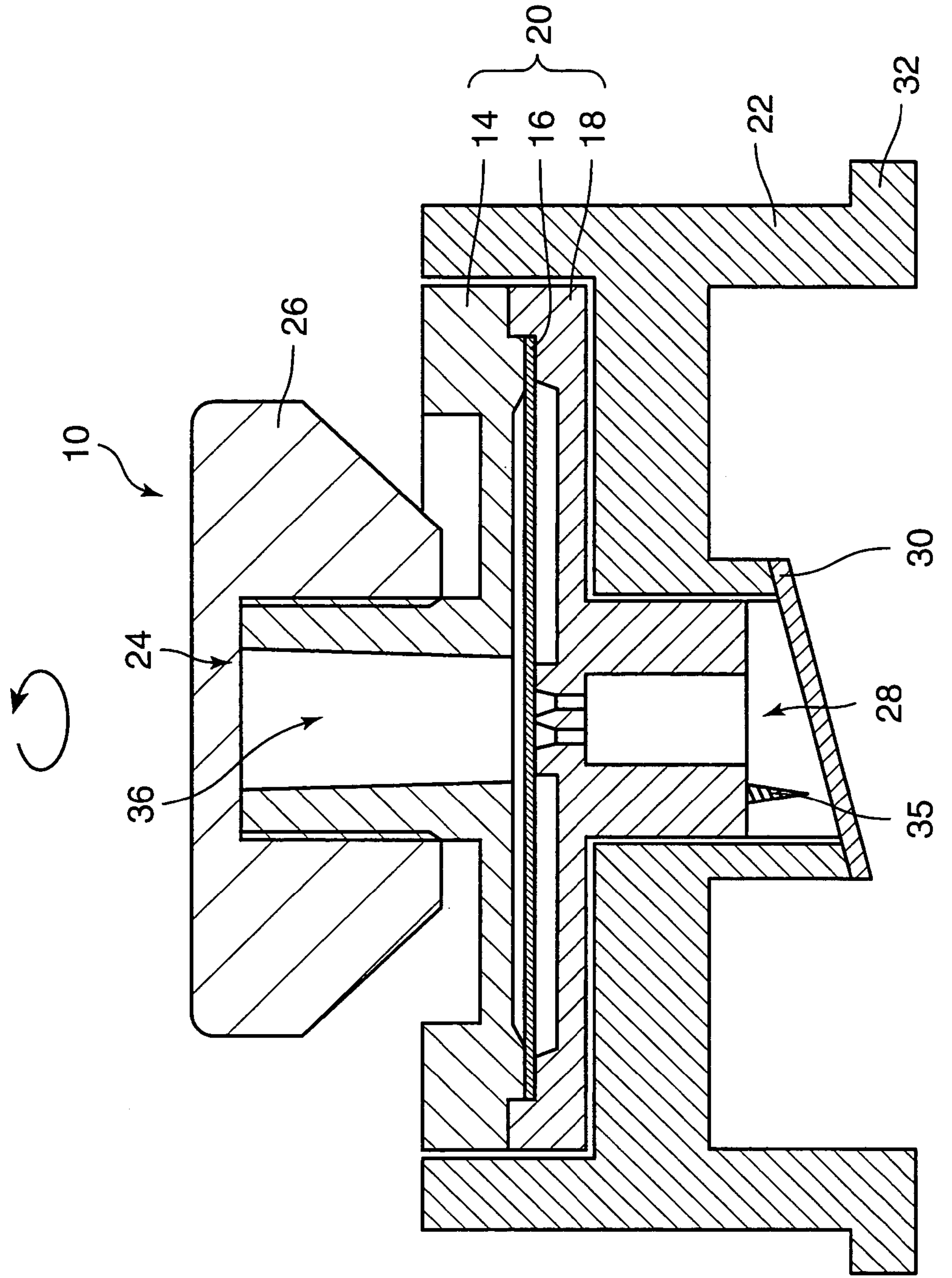
FIG. 18 is a longitudinal sectional view of still another liquid-medicine injection port device according to the present invention.

In the liquid-medicine injection port device 10 shown in FIG. 18, the liquid-medicine outlet 28 is blocked with the inclined closure film 30. At the bottom of the main-body member 20, a pin 35 is disposed downward on the side where the film 30 is further away from it. Thus, if the main-body member 20 is turned, the pin 35 hits on the closure film 30 and breaks it to open the liquid-medicine outlet 28.

Figure 19A:
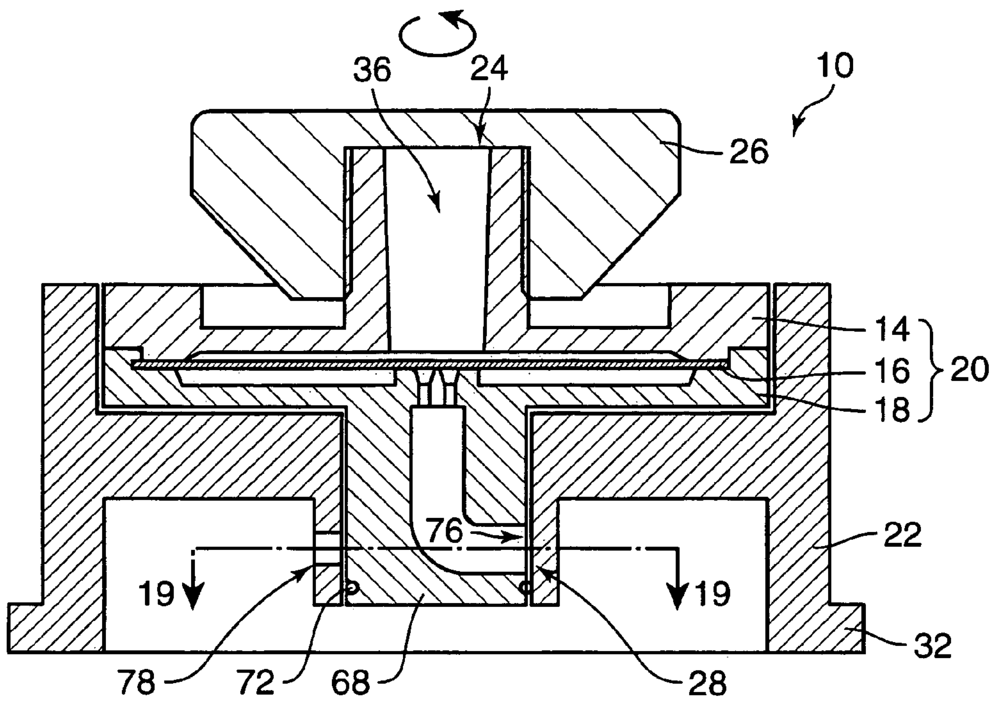
FIG. 19A being a longitudinal sectional view of the whole injection port device.
Figure 19B:
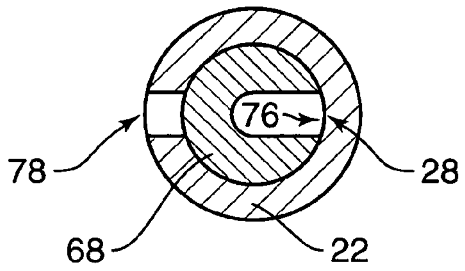
FIGS. 19B and 19C being sectional views, seen along the line 19-19 in FIG. 19A.
Figure 19C:
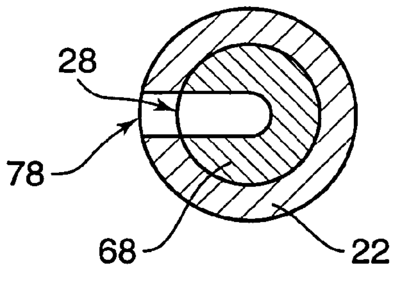

In the liquid-medicine injection port device 10 shown in FIG. 19, the main-body member 20 formed by the inlet member 14, the germ-removal filter 16 and the outlet member 18 can turn along the interior surface of the cylindrical member 22. The liquid-medicine outlet 28 is formed in the side of the hanging portion 68 of the outlet member 18. The liquid-medicine outlet 28 turns with keeping in contact with a rubbing surface 76. In a part of the rubbing surface 76 is provided an opening portion 78 which leads to the outside. Hence, before it is used, a turning position of the liquid-medicine outlet 28 is determined so that it is covered with the rubbing surface 76 (refer to FIG. 19B). When it is used, the main-body member 20 is turned so that the liquid-medicine outlet 28 and the opening portion 78 can meet (refer to FIG. 19C). Before it is used, the liquid-medicine outlet 28 is closed, thereby preventing the liquid medicine stored in the liquid-medicine container 12 (refer to FIG. 2) from going into the liquid-medicine injection port device 10. Injection-mixing is conducted by turning the main-body member 20, removing the cap 26 and injecting the liquid medicine from the liquid-medicine inlet 24 with a syringe or the like.

Figure 20:
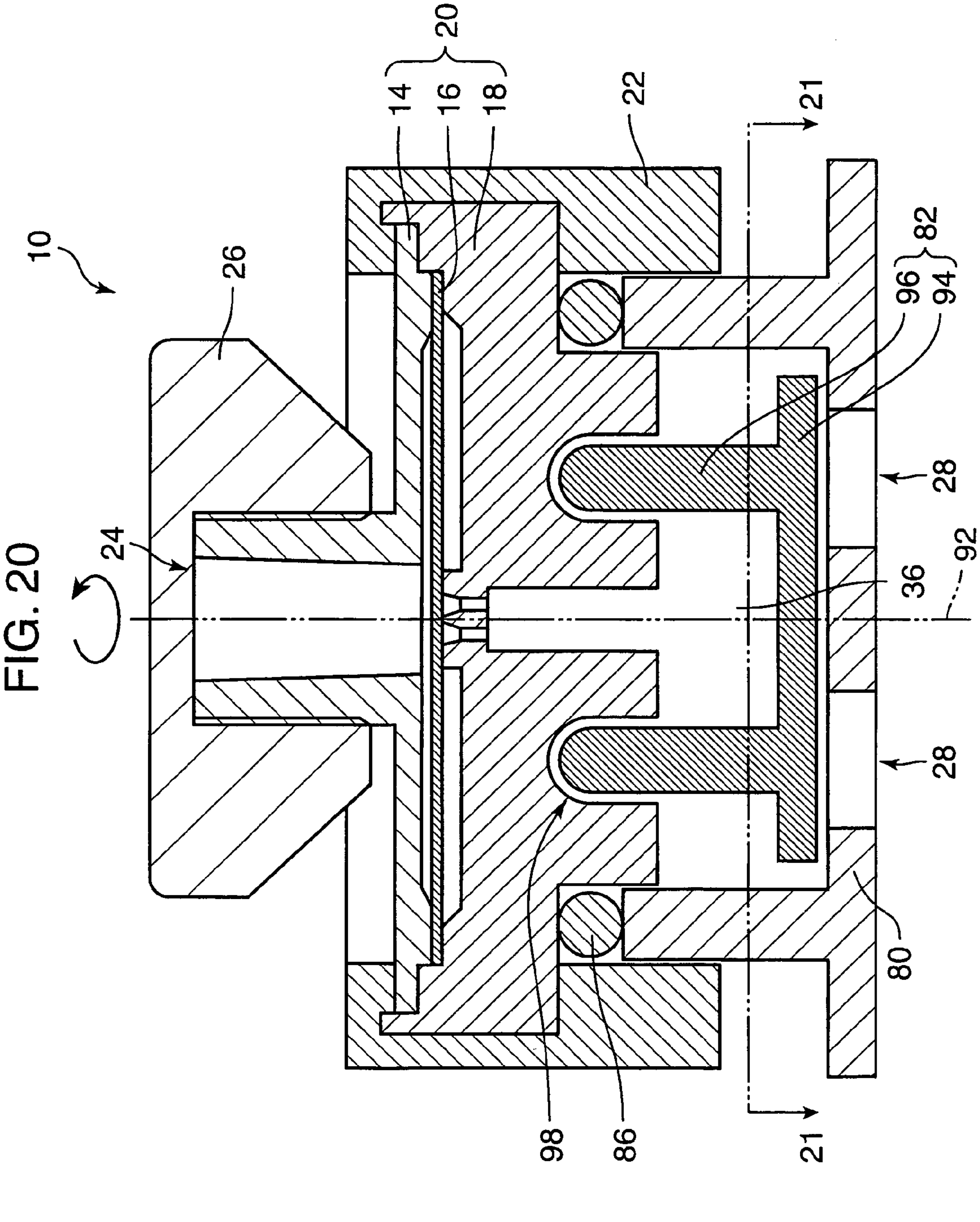
FIG. 20 is a longitudinal sectional view of still another liquid-medicine injection port device according to the present invention.

In the liquid-medicine injection port device 10 shown in FIG. 20, a cup-shaped bottom member 80 is provided underneath the outlet member 18. It and the outlet member 18 form the broad and relatively-spacious liquid passageway 36. In this liquid passageway 36, an inner-lid member 82 is provided which engages with the main-body member 20 so as to turn together with the main-body member 20. In the bottom member 80, two liquid-medicine outlets 28 are formed which are in contact with the lower surface of the inner-lid member 82 and that are away from a turning-center axis 92 of the main-body member 20.

Figure 21A:
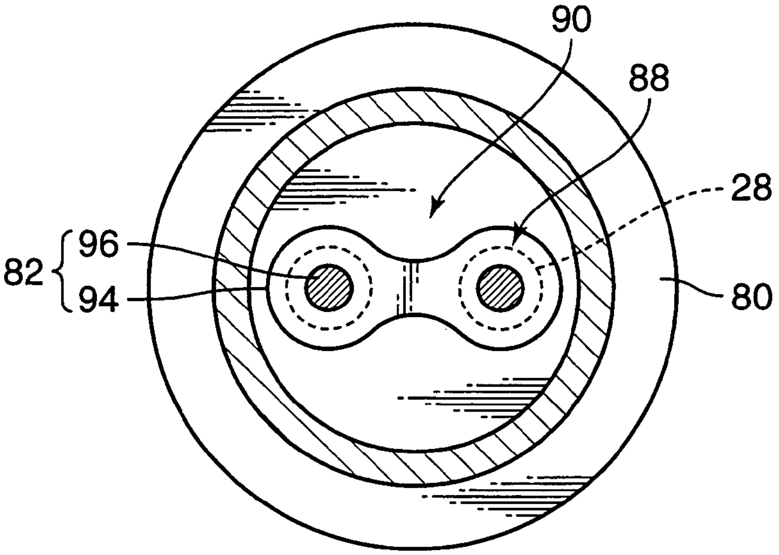
FIG. 21A showing a state in which a liquid-medicine outlet is closed, and FIG. 21B showing a state in which the liquid-medicine outlet is opened.
Figure 21B:
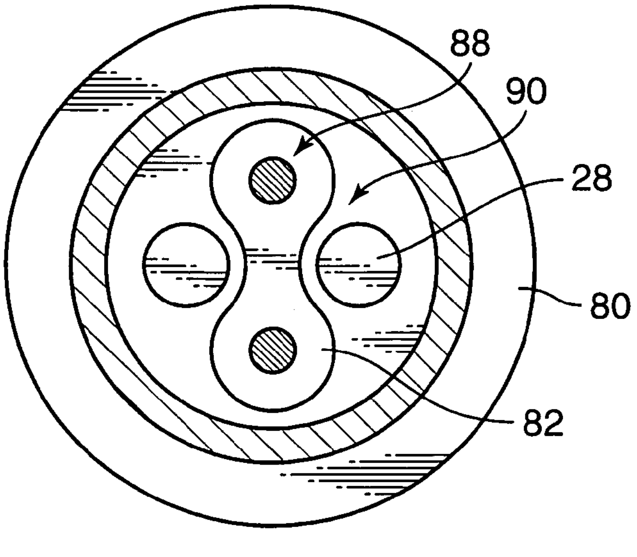
FIG. 21 is a sectional view, seen along the line 21-21 in FIG. 20, according to the present invention.

As shown in FIG. 21, the inner-lid member 82 has a flat-plate portion 94 which is shaped like substantially a pair of dumbbells, and two pole-shaped pillars 96 which is erected from it. The flat-plate portion 94 has two substantially-circular blind parts 88 on both its sides and has an arrow part 90 in the middle. Before the liquid-medicine injection port device 10 is used, the liquid-medicine outlets 28 formed in the bottom member 80 are covered with the blind parts 88. When it is used, however, the inner-lid member 82 is turned by an angle of 90 degrees to move the blind parts 88, thereby opening the liquid-medicine outlets 28. The two pole-shaped pillars 96 of the inner-lid member 82 are inserted into two holes 98 formed in the outlet member 18 to engage with them. Thus, they are turned along with the main-body member 20 united with the cylindrical member 22, as it is turned.

In this embodiment, the lower surfaces of the blind parts 88 of the inner-lid member 82 which cover the liquid-medicine outlets 28 may also be melted and attached, or glued, to the upper surface of the bottom member 80, at such a strength that it is peeled when you turn the main-body member 20 manually. Furthermore, the flat-plate portion 94 of the inner-lid member 82 may also be circular which has two openings leading to the liquid-medicine outlets 28. Alternatively, the cylindrical member 22 and the bottom member 80 may also be united, so that only the main-body member 20 and the inner-lid member 82 can be turned. Alternatively, three or more liquid-medicine outlets 28 may also be formed. In that case, the inner-lid member 82 is produced which can open and close all those liquid-medicine outlets 28.

Figure 22:
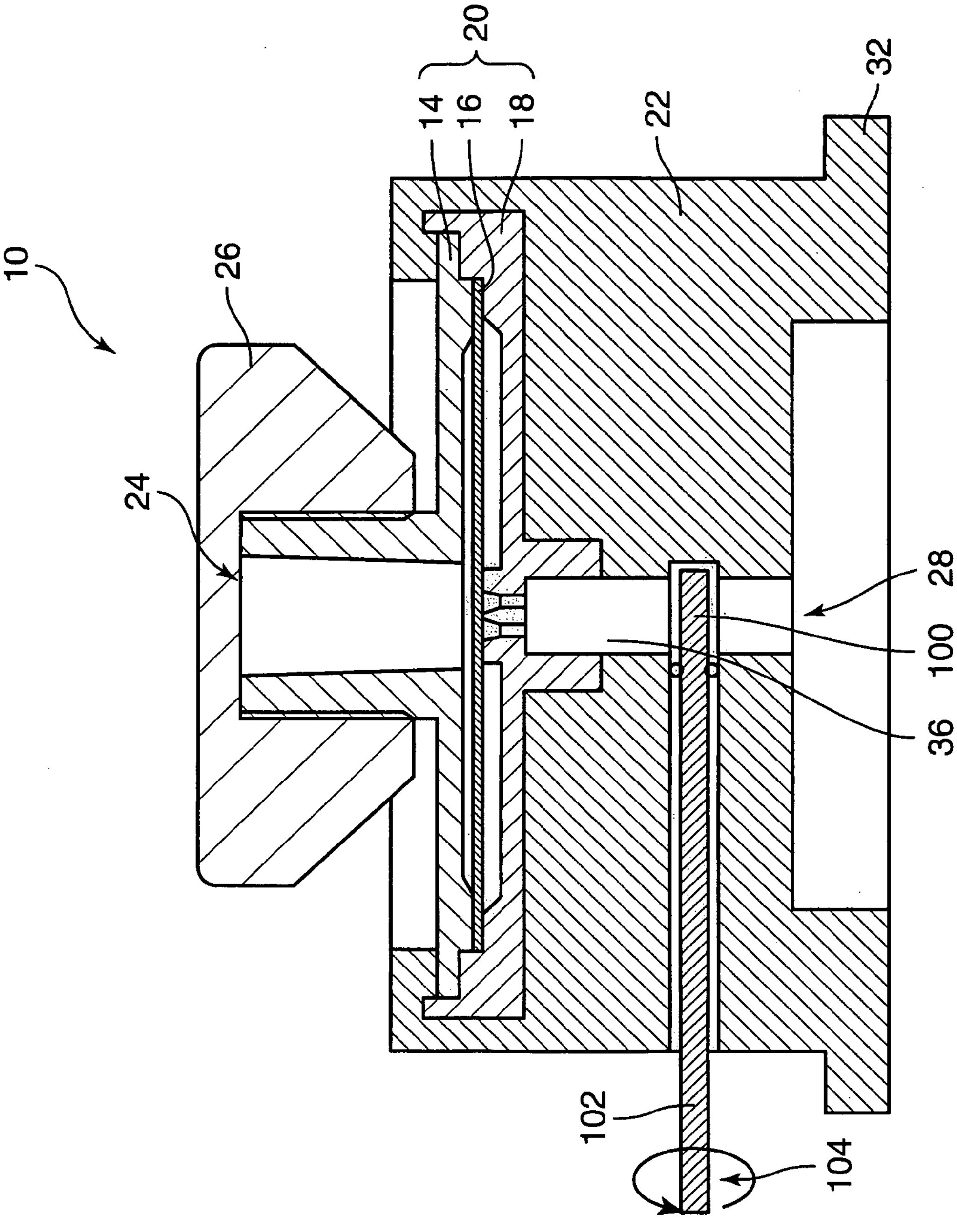
FIG. 22 is a longitudinal sectional view of still another liquid-medicine injection port device according to the present invention.
Figure 23:
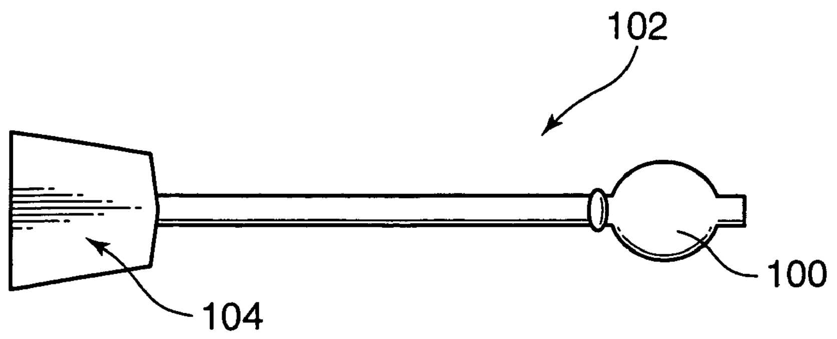
FIG. 23 is a top view of an operation member in FIG. 22, according to the present invention.
Figure 24:
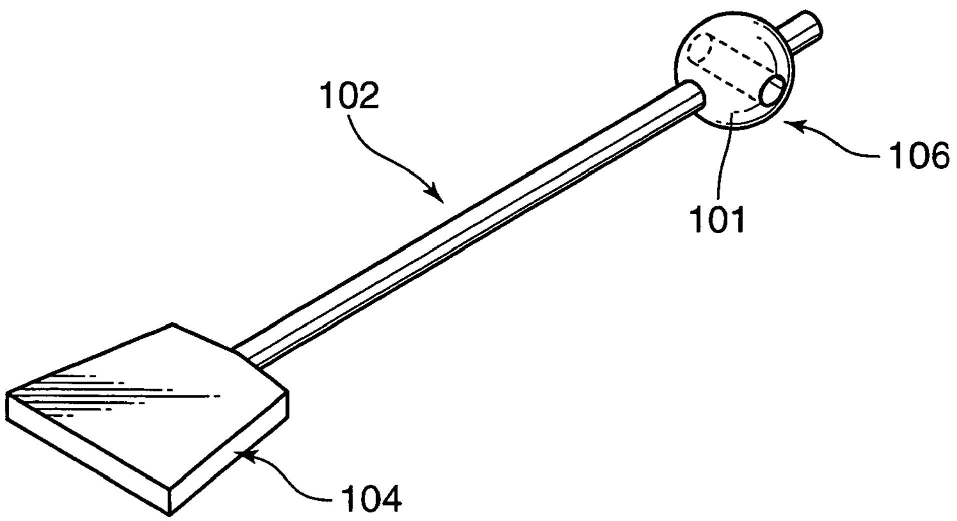
FIG. 24 is a perspective view of another operation member in FIG. 22, according to the present invention.

The liquid-medicine injection port device 10 shown in FIG. 22 is an example in which an open-and-close valve 100 which blocks the liquid passageway 36 is used as the closure. FIG. 23 shows an operation member 102 used in this liquid-medicine injection port device 10. The open-and-close valve 100 is shaped like a disk so that its cross section has the same configuration as that of the liquid passageway 36. In the same way as a butterfly valve, it is turned by an operation of the operation member 102, which penetrates the side part of the cylindrical member 22 and is connected to the open-and-close valve 100. At the end of the operation member 102 is formed a flat lever part 104. This enables to confirm whether the open-and-close valve 100 is opened or closed, and thus, to open and close it unfailingly and precisely. Furthermore, in the liquid-medicine injection port device 10 according to this example, such a spherical open-and-close valve 101 may be used as shown in FIG. 24. In the open-and-close valve 101, a liquid-passage hole 106 is formed which penetrates its spherical center. If it is turned by an angle of 90 degrees, the liquid passageway 36 can be opened or closed.

Figure 25:
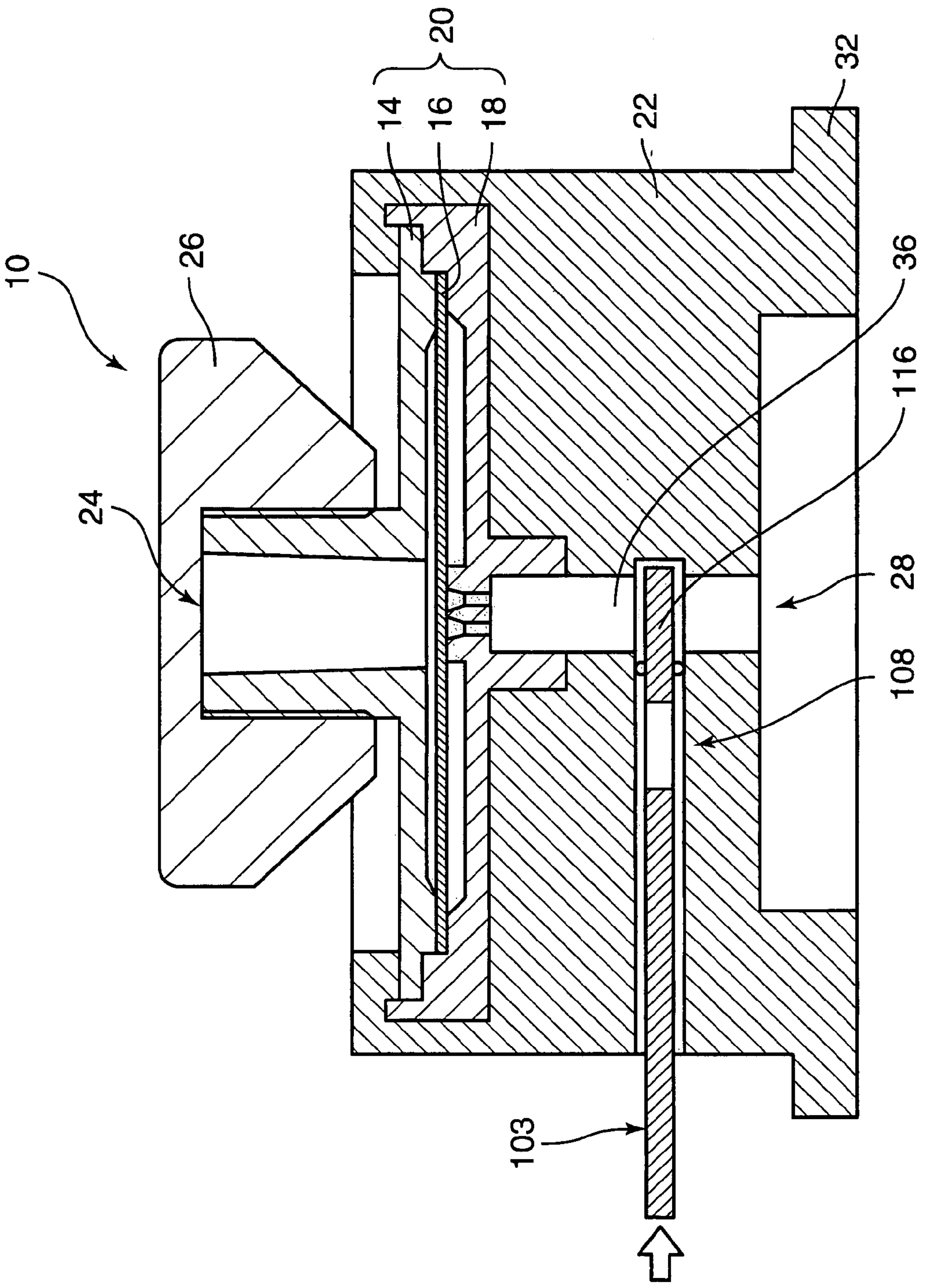
FIG. 25 is a longitudinal sectional view of still another liquid-medicine injection port device according to the present invention.
Figure 26:
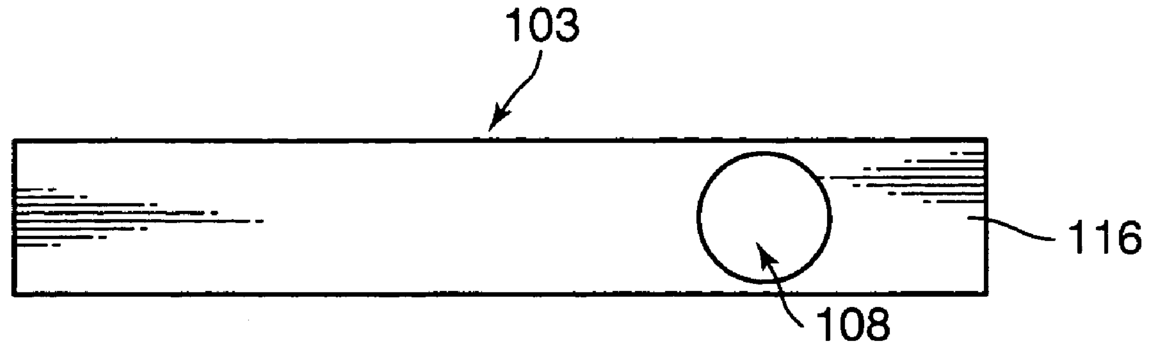
FIG. 26 is a top view of an operation member in FIG. 25, according to the present invention.

The liquid-medicine injection port device 10 shown in FIG. 25 is another example in which an open-and-close valve which blocks the liquid passageway 36 is used as the closure. FIG. 26 shows an operation member 103 used in this liquid-medicine injection port device 10. In this example, the open-and-close valve is used which is opened by sliding of the operation member 103 crossing the liquid passageway 36. In the strip-shaped operation member 103, a circular liquid-passage hole 108 is formed substantially at an end thereof. Before it is used (or injection-mixing is conducted), the liquid passageway 36 is blocked with a flat-plate portion 116 which is closer to the end of the operation member 103 than the liquid-passage hole 108. When it is used, the operation member 103 is pushed in, so that the liquid-passage hole 108 can be brought to the liquid passageway 36 to open the liquid passageway.

Figure 27:
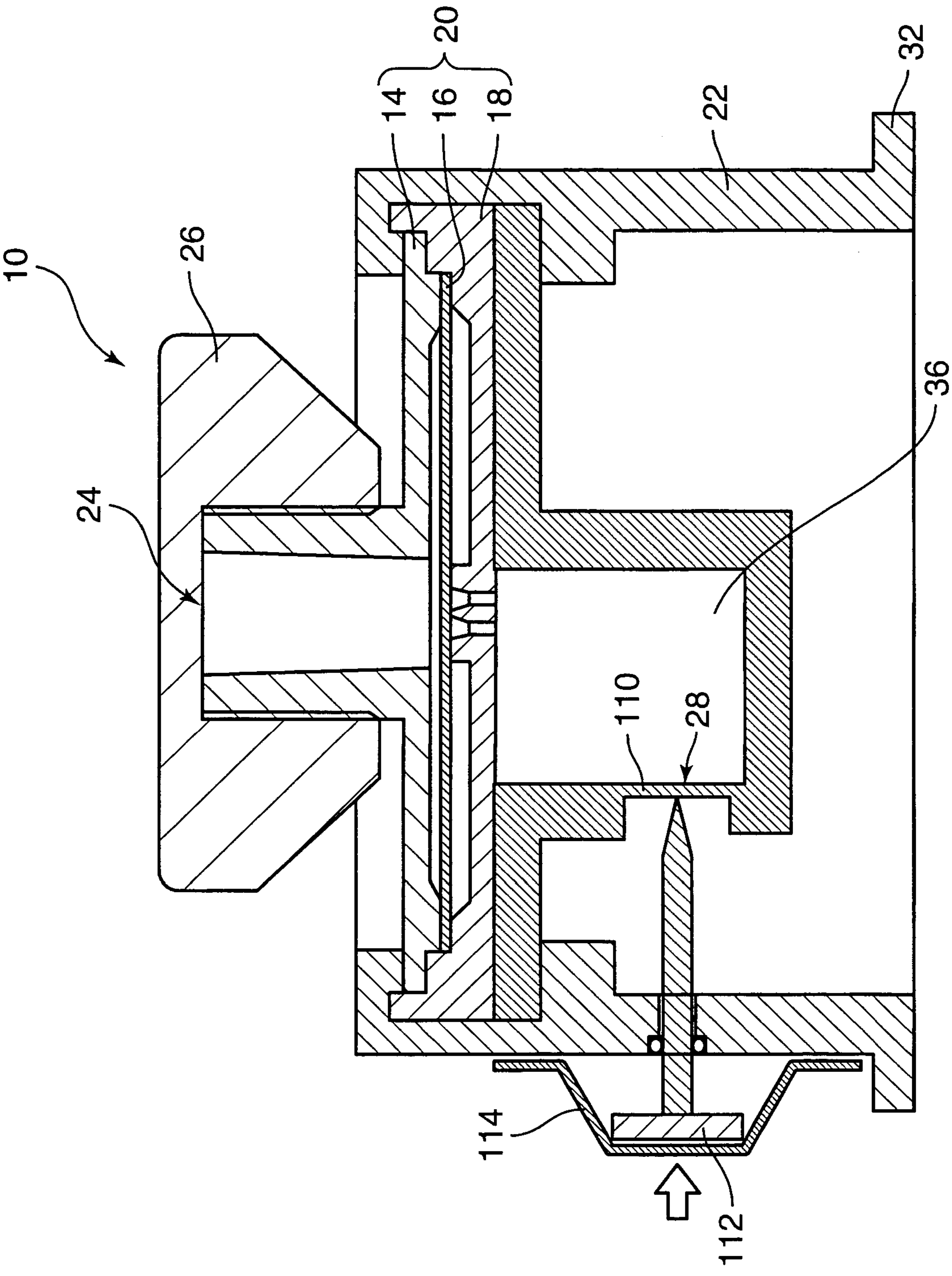
FIG. 27 is a longitudinal sectional view of still another liquid-medicine injection port device according to the present invention.

In the liquid-medicine injection port device 10 shown in FIG. 27, a means is used by which a partition wall 110 which blocks the liquid-medicine outlet 28 is broken by an operation of an operation member 112 which penetrates the side part of the cylindrical member 22, and thus, the liquid passageway 36 is opened. Specifically, the thin partition wall 110 closes a part which is the side part of the liquid passageway 36 and where the liquid-medicine outlet 28 is to be formed. Then, this partition wall 110 is broken through with the tip of the operation member 112. The tip of the operation member 112 is sharply pointed and faces the partition wall 110. If its rear end protruding from the cylindrical member 22 is pushed in, then the partition wall 110 can be broken easily. Herein, the rear end of the operation member 112 and its periphery are covered with a protective film 114, thereby preventing germs or the like from getting mixed inside.

Next, the liquid-medicine container 12 according to the present invention will be described in detail. In one of its embodiments is provided with some of the above described liquid-medicine injection port devices 10. Where or how the liquid-medicine injection port device 10 is attached is not limited especially. For example, it can be attached to the end or center of the liquid-medicine container 12. The liquid-medicine injection port device 10 may be attached to the main body of the liquid-medicine container 12, preferably, by melting-attachment, gluing or the like.

Figure 28:
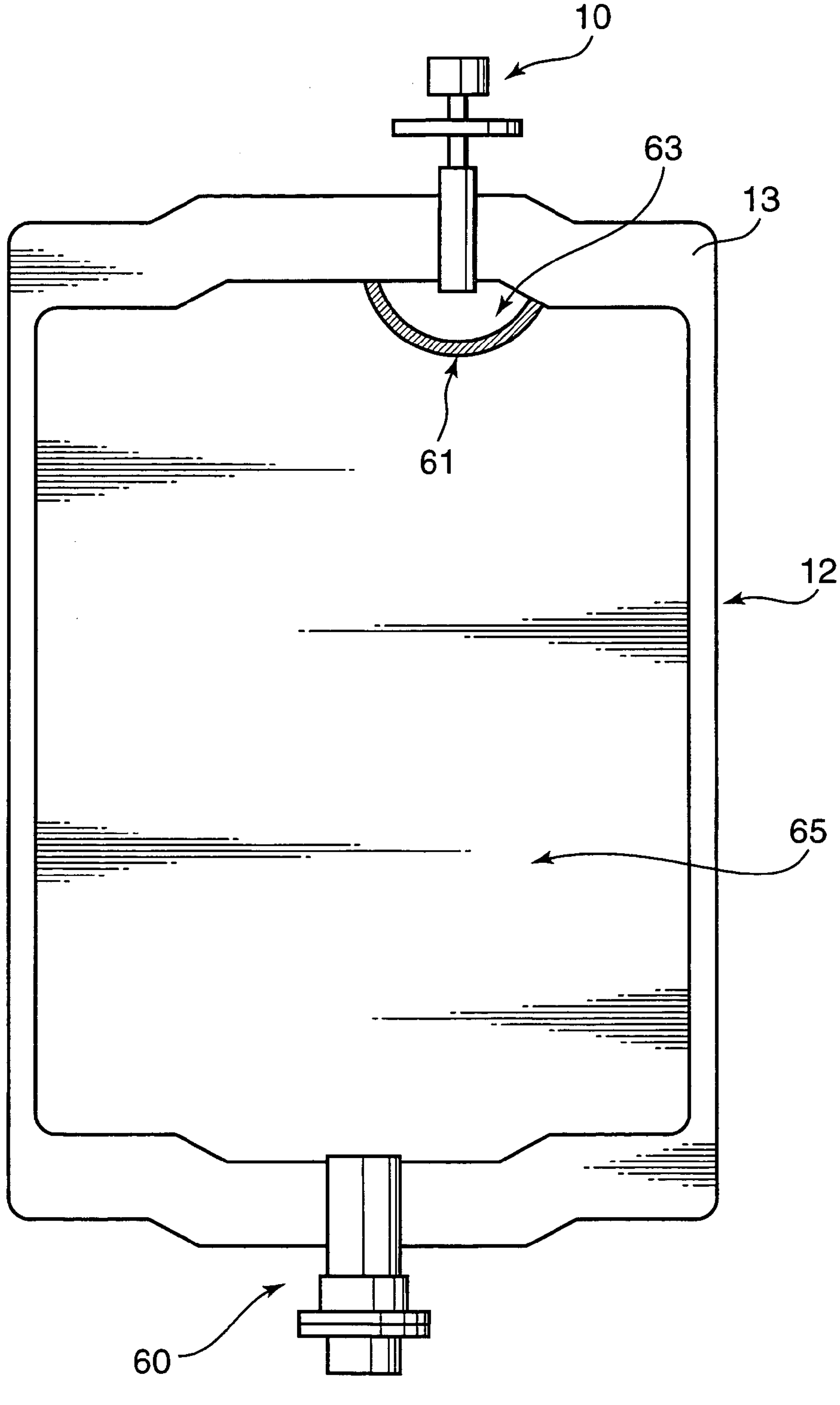
FIG. 28 is a front view of another liquid-medicine container according to the present invention.

FIG. 28 shows another embodiment of the liquid-medicine container 12 according to the present invention. Specifically, the liquid-medicine container 12, which includes the liquid-medicine injection port device 10 and the liquid-medicine discharge port device 60 which the germ-removal filter 16 (omitted in the figure) is attached to, is provided with two front and back sheets, and is shaped like a bag, in which: an injection chamber 63 provided with the liquid-medicine injection port device 10 and a storage chamber 65 storing a liquid medicine in advance are divided by a weak seal portion 61 which is formed by melting and attaching, or gluing, the two front and back sheets to each other at such a strength that they can be easily peeled. The weak seal portion 61 prevents the liquid medicine stored in the storage chamber 65 from going into the liquid-medicine injection port device 10. This keeps the germ-removal filter 16 from deteriorating, clogging up or the like, thereby maintaining the capability of the germ-removal filter 16 normally. When the liquid-medicine container 12 is used, the weak seal portion 61 is peeled so that the injection chamber 63 leads to the storage chamber 65. This allows injection-mixing to be easily conducted.

Figure 29:
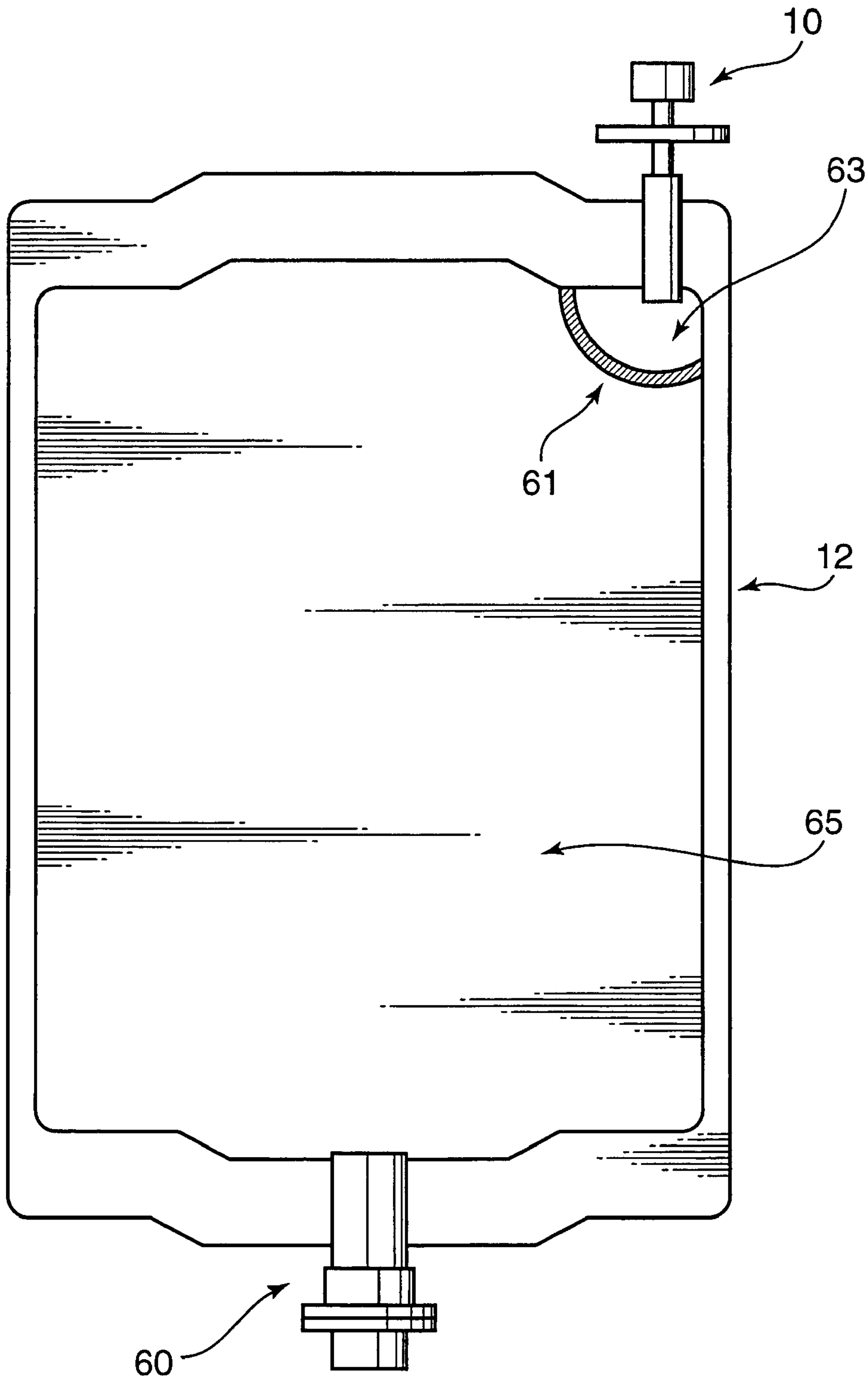
FIG. 29 is a front view of still another liquid-medicine container according to the present invention.

The means of peeling the weak seal portion 61 is not limited especially, but preferably, it should be peeled automatically by a liquid-medicine injection pressure. Therefore, in the embodiment especially useful according to the present invention, the weak seal portion 61 is melted and attached, or glued, at such a strength that it is peeled by receiving a liquid-medicine injection pressure. In the liquid-medicine container 12 shown in FIG. 29, the liquid-medicine injection port device 10 is in the corner of the liquid-medicine container 12. This makes it possible to shorten the weak seal portion 61 and make the injection chamber 63 small. Thereby, a liquid-medicine injection pressure is strongly applied on the weak seal portion 61, so that it is more certainly peeled.

Figure 30:
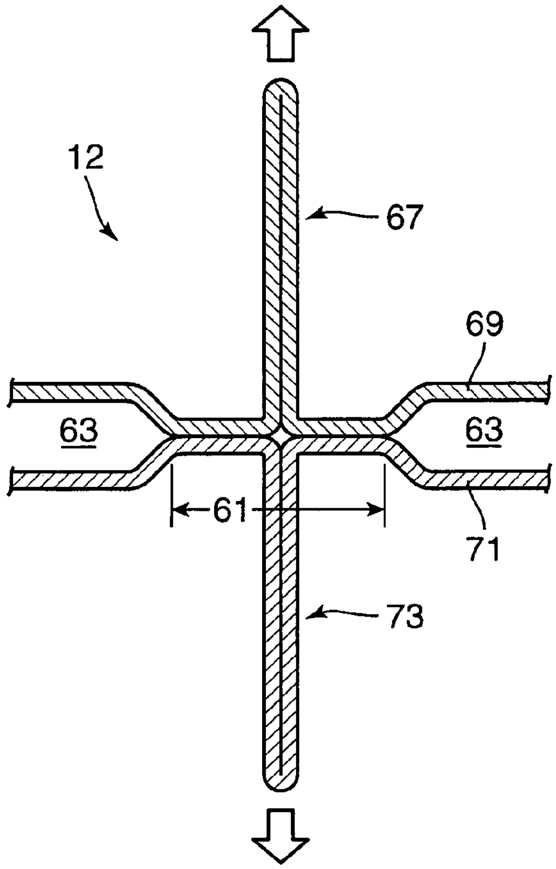
FIG. 30 is a sectional view of a weak seal portion according to the present invention.

Some projections are also effective in peeling the weak seal portion 61. For example, a projection for picking up and pulling may be formed in either or both of the front and back surfaces of the weak seal portion 61. In the weak seal portion 61 shown in FIG. 30, projections 67 are formed for each of the front and back sheets. These projections 67 are formed by slackening a front sheet 69 and a back sheet 71, and oppositely folding each of them in two. If the two projections 67 are picked up and pulled, then the weak seal portion 61 is easily peeled and separated into the front sheet 69 and the back sheet 71. This allows the injection chamber 63 to lead to the storage chamber 65.

Figure 31:
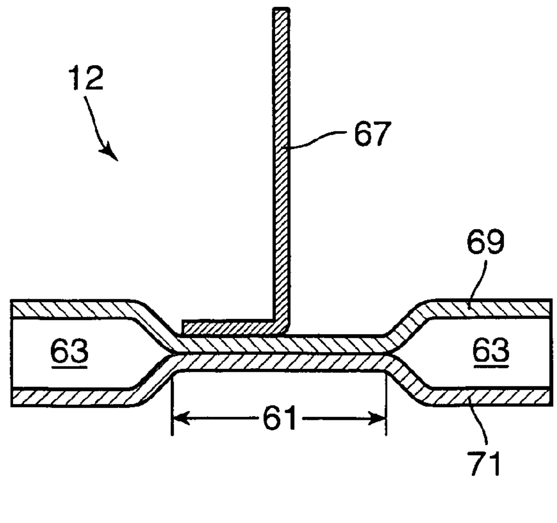
FIG. 31 is a sectional view of another weak seal portion according to the present invention.

In the weak seal portion 61 shown in FIG. 31, the projection 67 is provided only for the front surface. The projection 67 is a member which is separated from the front sheet 69 or the back sheet 71. It is fixed on the front sheet 69, by melting-attachment, gluing or the like. The shape or material quality of the projection 67 is not limited especially. However, a plastic sheet is preferably used, because it is easily fixed on the front sheet 69, and is also foldable, which helps it be conveniently housed.

Hereinbefore, the liquid-medicine injection port device and the liquid-medicine container which this is attached to according to the present invention have been described in detail. However, the present invention is not limited to the above described citations and illustrations. The shape or configuration of the liquid-medicine injection port device, the material quality of the inlet member, the outlet member, the bottom member, the cap or the like, the type or configuration of the germ-removal filter, the method of attaching the liquid-medicine injection port device to the liquid-medicine container, the type or configuration of the liquid-medicine container, the type or quantity of a liquid medicine, the method of sterilization, or the like, can be implemented from aspects including various improvements, modifications and variations, based on the knowledge of those skilled in the art, within the scope which does not depart from the spirit of the present invention.

For example, the shape of the liquid-medicine container is not limited to a rectangle, e.g., it may also be an ellipse or the like. In addition, the position in which the liquid-medicine injection port device is attached is not limited to the edge of the liquid-medicine container, e.g., it may also be attached to the side thereof. Besides, the weak seal portion may also be peeled by applying pressure on it by compulsion via the storage chamber. Furthermore, as a similar structure to the liquid-medicine injection port device 10 shown in FIG. 16, the closure film 30 may also be peeled, not by turning the main-body member 20, but by pulling up the main-body member 20.

INDUSTRIAL APPLICABILITY

In the liquid-medicine injection port device according to the present invention, a germ-removal filter is provided, thereby making injection-mixing safe. This is because even if germs or the like get mixed into a liquid medicine to be injected for the injection-mixing, they are removed with the germ-removal filter, and then, the liquid medicine goes into the liquid-medicine container. Furthermore, a closure is provided which blocks the liquid passageway downstream from the germ-removal filter. This prevents a liquid medicine stored in the liquid-medicine container from going into the liquid-medicine injection port device before its use. Thereby, the germ-removal filter is kept from deteriorating, clogging up or the like, and thus, the capability of the germ-removal filter 16 is normally maintained. Furthermore, the closure is easily opened, allowing it to be used (or injection-mixing to be conducted) conveniently by a simple operation.

Furthermore, the closure is opened by a liquid-medicine injection pressure. Hence, the liquid-medicine injection port device can be obtained which is capable of conducting injection-mixing easily, simply by injecting a liquid medicine. In other words, there is no need to conduct any other operation.

Furthermore, the closure is opened by a movement of the main-body member. Accordingly, there is no need for any new members which open the main-body member. This allows the liquid-medicine injection port device to have a simple structure.

Furthermore, the closure is an open-and-close valve which is opened by an operation of the operation member which penetrates the side wall of the liquid-medicine injection port device. Hence, the liquid-medicine injection port device can be obtained which is capable of opening the closure surely.

Furthermore, in the liquid-medicine container which is provided with the liquid-medicine injection port device according to the present invention, injection-mixing can be conducted by an easy operation, and a safe liquid medicine which does not include any germs or the like can be obtained. This makes it possible to give it to a patient at ease, without worrying about any side effects such as septicemia and endotoxin shock.

The invention claimed is:

1. A liquid-medicine injection port device, comprising:

an inlet member having a liquid-medicine inlet which is formed at an upper end thereof;

an outlet member having a liquid-medicine outlet which is formed at a lower end thereof, the liquid-medicine outlet being dimensioned and configured to be connected to an inside of a liquid-medicine container;

a liquid passageway which connects the liquid-medicine inlet and the liquid-medicine outlet;

a germ-removal filter which is provided in the liquid passageway; and a closure which closes the liquid passageway underneath the germ-removal filter, wherein:

a cross-sectional area of the liquid passageway near the liquid-medicine outlet is smaller than a cross-sectional area of the liquid passageway just above the germ-removal filter; and the closing by the closure is opened by injection pressure of a liquid medicine which is injected from the liquid-medicine inlet of the inlet member.

2. The liquid-medicine injection port device according to claim 1, wherein the closure is a film which blocks the liquid passageway; and the film has a weak part which is broken by a liquid-medicine injection pressure.

3. The liquid-medicine injection port device according to claim 1, wherein the closure is a film which blocks the liquid-medicine outlet; the film is melted and attached, or is glued, to the periphery of the liquid-medicine outlet to cover the liquid-medicine outlet; and the strength of the melting-attachment or gluing is such a degree that the film is peeled by a liquid-medicine injection pressure.

4. The liquid-medicine injection port device according to claim 1, wherein the closure is an elastic member which blocks the liquid-medicine outlet; and the elastic member is deformed by receiving a liquid-medicine injection pressure to open the liquid-medicine outlet.

5. The liquid-medicine injection port device according to claim 1, wherein the closure is a closure member which is inserted into the liquid-medicine outlet; and the closure member clings to the inside of the liquid-medicine outlet, at such a strength that it comes off the liquid-medicine outlet by a liquid-medicine injection pressure.

6. The liquid-medicine injection port device according to claim 5, further comprising a means for receiving the closure member that comes off the liquid-medicine outlet when a liquid medicine is injected.

7. The liquid-medicine injection port device according to claim 1, wherein the liquid-medicine inlet is sealed up with a rubber elastic body which is pierced with an injection needle to form a liquid-medicine storage space between the liquid-medicine inlet and the germ-removal filter; a compressor is provided which compresses the inner volume of the liquid-medicine storage space; and the liquid-medicine injection pressure of a liquid medicine which is once injected into the liquid-medicine storage space is heightened by the compressor to compressively send the liquid medicine to the side of the germ-removal filter.

8. A liquid-medicine-injection port device-attached liquid-medicine container, comprising the liquid-medicine injection port device according to claim 1.

* * * * *